(12) United States Patent
Prakash et al.

(10) Patent No.: US 9,115,166 B2
(45) Date of Patent: Aug. 25, 2015

(54) REBAUDIOSIDE A DERIVATIVE PRODUCTS AND METHODS FOR MAKING

(75) Inventors: Indra Prakash, Alpharetta, GA (US); Grant E. DuBois, Roswell, GA (US); Rafael I. San Miguel, Atlanta, GA (US); John Clos, Lithia Springs, GA (US)

(73) Assignee: The Coca-Cola Company, Atlanta, GA (US)

( * ) Notice: Subject to any disclaimer, the term of this patent is extended or adjusted under 35 U.S.C. 154(b) by 295 days.

(21) Appl. No.: 12/392,439

(22) Filed: Feb. 25, 2009

(65) Prior Publication Data

US 2010/0278993 A1 Nov. 4, 2010

Related U.S. Application Data

(60) Provisional application No. 61/031,300, filed on Feb. 25, 2008, provisional application No. 61/140,646, filed on Dec. 24, 2008.

(51) Int. Cl.
*A23L 1/236* (2006.01)
*C07H 15/256* (2006.01)

(52) U.S. Cl.
CPC ............ *C07H 15/256* (2013.01); *A23L 1/2366* (2013.01)

(58) Field of Classification Search
CPC .................................................. A23L 1/2366
USPC .................................................. 536/5, 18.1
See application file for complete search history.

(56) References Cited

U.S. PATENT DOCUMENTS 4,353,889 A  10/1982  Dubois

FOREIGN PATENT DOCUMENTS

| CN | 1459245 A | 12/2003 |
| JP | 52083731 A | 12/1977 |
| JP | 04046190 A | 2/1992 |
| WO | WO 2007061795 A1 | 5/2007 |
| WO | WO 2007070224 A2 | 6/2007 |
| WO | WO 2009038978 A2 | 3/2009 |

OTHER PUBLICATIONS

Kinghorn, et al., Medicinal Research Review, 1989, 9, 91-115.*

Chang et al, "Stability Sudies of Stevioside and Rebaudioside A in Carbonated Beverages", J. Agric. Food Chem. 1983, vol. 31, pp. 409-412.*

Kobayashi, M., et al., "Dulcosides A and B, new diterpene glycosides from *Stevia rebaudiana*", Phyto-chemistry, 1977, vol. 16(1): 1405-1408.

Mosettig, E., et al., "The Absolute Configuration of Steviol and Isosteviol", J. Am. Chem. Soc. 2002, vol. 85(15): 2305-2309.

Mosettig, E., et al., "A Direct Correlation of the Diterpene Alkaloids and Hydrocarbons of the Phyllo-cladene Group, Interconversion of Garryfoline and Steviol", J. Am. Chem. Soc. 1961, vol. 83(14): 3163-3164.

Kos, O., et al., "Ent-kaurane glycosides and sesquiterpene lactones of the hirsutinole type from *Veronia triflosculosa*", Phytochemistry, 2006, vol. 67(1): 62-69.

Kamiya, S., et al., "Synthesis and Taste of Some Analogs of Stevioside," Agric. Biol. Chem. 1979, vol. 43(9): 1863-1879.

Ryoji, K., et al., "Sweet Diterpene-Glycosides of Leaves of *Stevia rebaudiana* Bertoni Synthesis and Structure-Sweetness Relation of Rebaudiosides A, D, and E and Their Related Glycosides," Nippon Ka-gaku Kaishi: Journal of the Chemical Society of Japan, 1981, No. 5: 726-735 (English Abstract).

Ohtani, K., et al., "Minor Diterpene Glycosides from Sweet Leaves of *Rubus suavissimus*", Phytochem-istry, 1992, vol. 31(5): 1553-1559.

Boeck, P., et al., "A Simple Synthesis of Kaurenoic Esters and other Derivatives and Evaluation of their Antifungal Activity," *Journal of Brazilian Chemical Society*, vol. 16, pp. 1360-1366, 2005.

Darise, M., et al. "Enzymatic Transglucosylation of Rubusoside and the Structure-Sweetness Relation-ship of Steviol-Bisglycosides," *Agric. Biol. Chem.* vol. 48, No. 10, pp. 2483-2488, 1984.

Kasai, R., et al. "Sweet Diterpene-Glycosides of Leaves of *Stevie rebaudiana* Bertoni—Synthesis and Structure-Sweetness Relation-ship of Rebaudiosides-A, -D, -E and Their Related Glycosides," No. 5, pp. 726-735, 1981.

Orihara, Y., et al. "Biotransformation of Steviol by Cultured Cells of *Eucalyptus perriniana* and *Coffea* Arabzca," *Phytochemistry*, vol. 30, No. 12, pp. 3989-3992, 1991.

Wang, D., "Sweetness and Mechanism of Picnic in Stevioside," *China Food Additives*, vol. 3, pp. 46-53, 2007.

Clos, J., et al. "Photostability of Rebaudioside A and Stevioside in Beverages," *J. Agric. Food Chem.*, vol. 56, No. 18, pp. 8507-8513, 2008.

* cited by examiner

*Primary Examiner* — Elli Peselev

(74) *Attorney, Agent, or Firm* — King & Spalding

(57) ABSTRACT

Exemplary embodiments of this invention encompass a method for degrading rebaudioside A and the rebaudioside A derivative products derived therefrom. In particular, this invention relates to a method for degrading rebaudioside A compositions to obtain rebaudioside A derivative products suitable for use as sweetener compositions.

9 Claims, No Drawings

REBAUDIOSIDE A DERIVATIVE PRODUCTS AND METHODS FOR MAKING

CROSS-REFERENCE TO RELATED APPLICATIONS

The present application claims the benefit of priority under 35 U.S.C. §119(e) to U.S. Provisional Application No. 61/031,300, filed Feb. 25, 2008, and to U.S. Provisional Application No. 61/140,646, filed Dec. 24, 2008, the disclosures of which are incorporated herein by reference in their entirety.

FIELD OF INVENTION

This invention relates generally to derivative products of rebaudioside A and methods for preparing derivative products of rebaudioside A.

BACKGROUND OF INVENTION

Rebaudioside A is a high-potency diterpenoid glycoside sweetener having the chemical structure:

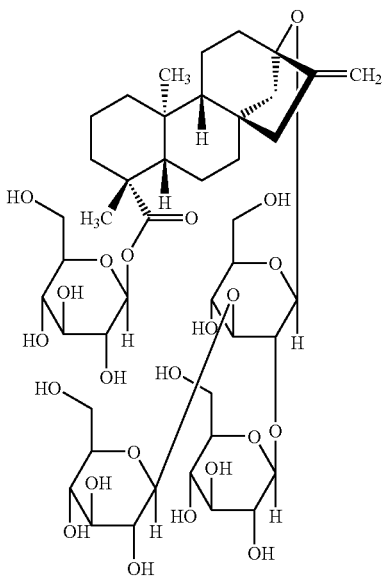

Rebaudioside A is isolated and extracted, along with other steviol glycosides, from the *Stevia rebaudiana* (Berton) plant ("*Stevia*"), which is commercially cultivated in Japan, Singapore, Taiwan, Malaysia, South Korea, China, Israel, India, Brazil, Australia, and Paraguay. It is a natural non-caloric sweetener with functional and sensory properties superior to those of many other non-caloric sweeteners. Processed forms of *Stevia* can be 70 to 400 times more potent than sugar; however, *Stevia* also has a bitter component. Of the four major diterpenoid glycoside sweeteners present in *Stevia*, rebaudioside A has been identified as the least astringent, the least bitter, and with the least persistent aftertaste. However, rebaudioside A still exhibits flavor and taste characteristics that distinguish it from sugar. Accordingly, it may be desirable to modify rebaudioside A to obtain novel compounds useful as sweetening compositions but exhibiting more desirable flavor and/or temporal profiles than rebaudioside A.

SUMMARY OF INVENTION

Exemplary embodiments of the invention address the above-identified need by providing a method for preparing rebaudioside A derivative products useful as sweetening compositions and the rebaudioside A derivative products produced therefrom.

In particular, embodiments provided herein include a method for preparing rebaudioside A derivative products by heating a rebaudioside A solution with an inorganic acid at about 50 to about 110° C. for a time sufficient to complete the reaction and thereby obtain a rebaudioside A derivative product.

In other embodiments a sweetener is provided comprising a rebaudioside A derivative product. The rebaudioside A derivative product comprises a rebaudioside A derivative compound having the chemical formula I:

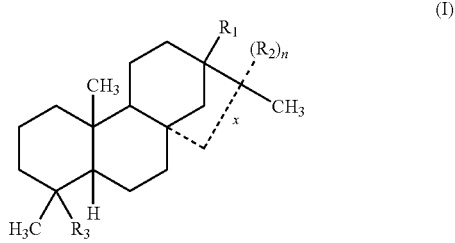

wherein $R_1$ may be a monosaccharide, an oligosaccharide comprising two or three sugars, an alkyl, or a hydroxyl;

wherein $R_2$ may be a hydrogen, hydroxyl, or alkoxy;

wherein $R_3$ may be a hydrogen, hydroxyl, alkoxy, alkenyl, alkynyl, a straight, chained, branched, or cyclic alkyl, alkenyl, or alkynyl, aryl, heteroaryl, heterocyclic, or acyl group which is substituted or unsubstituted;

wherein x may be a single bond or a double bond; wherein n is 0 or 1; and wherein when x is a single bond, n is 1, and $R_2$ may be a hydrogen, hydroxyl, or alkoxy; and wherein when x is a double bond, n is 0.

In a particular embodiment of the rebaudioside A derivative product of formula I, wherein x is a single bond and n is 1, the rebaudioside A derivative product comprises a rebaudioside A derivative compound having the chemical formula IA:

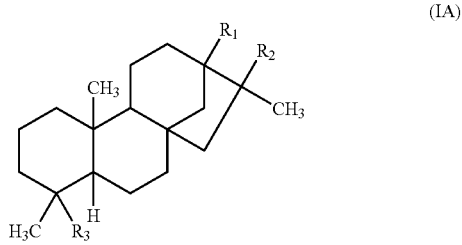

wherein $R_1$ may be a monosaccharide, an oligosaccharide comprising two or three sugars, an alkyl, or a hydroxyl;

wherein $R_2$ may be a hydrogen, hydroxyl, or alkoxy; and wherein $R_3$ may be a hydrogen, hydroxyl, alkoxy, alkenyl, alkynyl, a straight, chained, branched, or cyclic alkyl, alkenyl, or alkynyl, aryl, heteroaryl, heterocyclic, or acyl group which is substituted or unsubstituted.

In another particular embodiment of the rebaudioside A derivative product of formula I, wherein x is a double bond and n is 0, the rebaudioside A derivative product comprises a rebaudioside A derivative compound having the chemical formula IB:

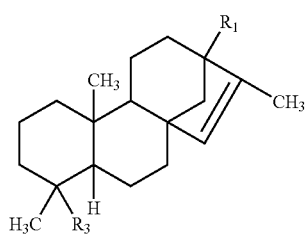

(IB)

wherein $R_1$ may be a monosaccharide, an oligosaccharide comprising two or three sugars, an alkyl, or a hydroxyl; and wherein $R_3$ may be a hydrogen, hydroxyl, alkoxy, alkenyl, alkynyl, a straight, chained, branched, or cyclic alkyl, alkenyl, or alkynyl, aryl, heteroaryl, heterocyclic, or acyl group which is substituted or unsubstituted.

In another embodiment, the rebaudioside A derivative product comprises a rebaudioside A derivative compound having the chemical formula:

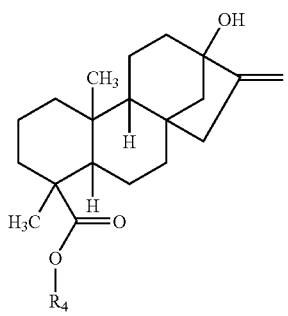

wherein $R_4$ may be a monosaccharide.

In still another embodiment, the rebaudioside A derivative product comprises a rebaudioside A derivative compound having the chemical formula:

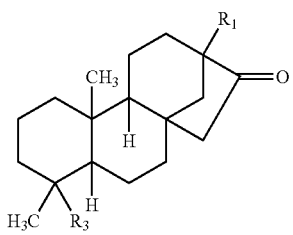

wherein $R_1$ may be a monosaccharide, an oligosaccharide comprising two or three sugars, an alkyl, or a hydroxy;

wherein $R_3$ may be a hydrogen, hydroxyl, alkoxy, alkenyl, alkynyl, a straight, chained, branched, or cyclic alkyl, alkenyl, alkynyl, aryl, heteroaryl, heterocyclic, or acyl group which is substituted or unsubstituted.

In still another embodiment, the rebaudioside A derivative product comprises a rebaudioside A derivative compound having the chemical formula:

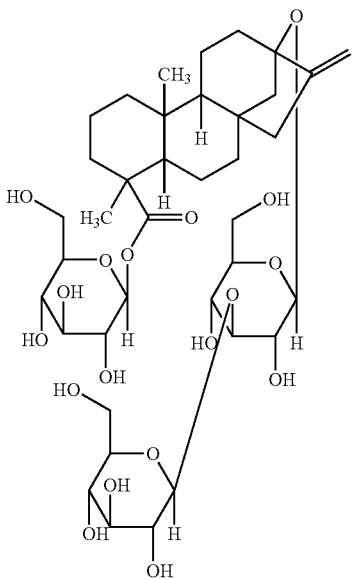

Other objects, features, and advantages of the invention will be apparent from the following detailed description, drawings, and claims. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

DETAILED DESCRIPTION OF INVENTION

Reference now will be made in detail to the presently proffered embodiments of the invention. Each example is provided by way of explanation of embodiments of the invention, not limitation of the invention. In fact, it will be apparent to those skilled in the art that various modifications and variations can be made in the present invention without departing from the spirit or scope of the invention. For instance, features illustrated or described as part of one embodiment, can be used on another embodiment to yield a still further embodiment. Thus, it is intended that the present invention cover such modifications and variations within the scope of the appended claims and their equivalents.

Briefly described, embodiments of the present invention include rebaudioside A derivative products and methods for preparing rebaudioside A derivative products. In particular, embodiments provided herein include rebaudioside A derivative products suitable for use as sweeteners.

I. Methods of Preparing Rebaudioside a Derivative Products

In a particular embodiment, a method of preparing a rebaudioside A derivative product is provided.

The method for preparing rebaudioside A derivative products generally comprises preparing a solution of either a crude or a substantially pure rebaudioside A composition comprising a rebaudioside A compound and an inorganic acid or base, heating or pressurizing, or a combination thereof, the solution to a temperature and pressure sufficient to react the rebaudioside A compound for a time sufficient to obtain a rebaudioside A derivative product, and recovering the rebaudioside A derivative product. In one embodiment, a temperature sufficient to react the rebaudioside A compound is in the range of about 50 to about 110° C., more particularly from about 65 to about 95° C., and still more particularly from about 75 to about 85° C. Any suitable means of heating known to those of ordinary skill in the art may be used to heat the solution, non-limiting examples of which include sunlight or elevated ambient temperatures. In one embodiment, a time sufficient to react the rebaudioside A compound is in the range of about 0.5 to about 24 hours.

Non-limiting examples of inorganic acids suitable for use in embodiments herein include phosphoric acid, phosphorous acid, polyphosphoric acid, hydrochloric acid, sulfuric acid, nitric acid, carbonic acid, sodium dihydrogen phosphate, and combinations thereof. Non-limiting examples of inorganic bases suitable for use in embodiments herein include sodium hydroxide, potassium hydroxide, sodium carbonate, potassium carbonate, magnesium carbonate, calcium carbonate and combinations thereof. Not wishing to be bound by any theory, it is believed that the use of an acid will result in the hydration of the alkene and/or cleaving of the ester while the use of a base will result in a saponification reaction requiring addition of an inorganic acid to reform the carboxylic acid.

As used herein, a crude rebaudioside A composition comprises purity levels of a rebaudioside A compound less than about 80% rebaudioside A compound by weight on a dry basis, at less than about 70% by weight on a dry basis, or at less than about 60% by weight on a dry basis.

As used herein, a substantially pure rebaudioside A composition comprises purity levels of a rebaudioside A compound equal to or greater than 80% rebaudioside A compound by weight on a dry basis up to about 100% by weight on a dry basis, greater than about 90% by weight on a dry basis, greater than about 97% A by weight on a dry basis, greater than about 98% by weight on a dry basis, or greater than about 99% by weight on a dry basis. Purity, as used here, represents the weight percentage of a rebaudioside A compound or rebaudioside A derivative compound, in raw or purified form. Methods of purifying crude rebaudioside A compound to obtain a substantially pure rebaudioside A composition are described herein below.

The resulting rebaudioside A derivative product generally comprises a mixture of a supernatant and a precipitate. In a particular embodiment, the step of recovering the rebaudioside A derivative product comprises isolating the supernatant, the precipitate, or a combination thereof. The rebaudioside A derivative product may be recovered using any suitable solid-liquid separation techniques. For example, the derivative product of the supernatant and precipitate may be isolated from each other by decanting the supernatant from the precipitate. Other separation techniques may utilize centrifugal force, non-limiting examples of which include vertical and horizontal perforated basket centrifuge, solid bowl centrifuge, decanter centrifuge, peeler type centrifuge, pusher type centrifuge, Heinkel type centrifuge, disc stack centrifuge and cyclone separation. In addition, separation of the rebaudioside A derivative product in the supernatant and precipitate may be enhanced by any of pressure, vacuum, and gravity filtration methods, that include, without limitation, the use of belt, drum, nutsche type, leaf, plate, Rosenmund type, sparkler type, and bag filters and filter press.

The recovered rebaudioside A derivative product of the supernatant optionally may be clarified with an aqueous organic solution while the recovered rebaudioside A derivative product of the precipitate optionally may be dissolved in an aqueous organic solution (e.g., methanol, ethanol, isopropanol, n-propanol or mixtures).

Those of ordinary skill in the art should appreciate that the rebaudioside A derivative product generally will not be in a purified form after its preparation. Accordingly, in particular embodiments, a rebaudioside A derivative product may comprise an amount from about 0.5% to about 50% by weight of the rebaudioside A derivative compound or any amount therebetween (i.e., from about 0.5% to about 45%, from about 0.5% to about 40%, from about 0.5% to about 35%, from about 0.5% to about 30%, from about 0.5% to about 25%, from about 0.5% to about 15%, from about 0.5% to about 10%, from about 0.5% to about 5%, and the like).

In other particular embodiments, the method of preparing a rebaudioside A derivative product further comprises purifying the rebaudioside A derivative product. For example, the rebaudioside A derivative product may be purified from the supernatant or precipitate by normal phase and/or reversed-phase column chromatography. Suitable columns for purifying the rebaudioside A derivative product may be determined by one of ordinary skill in the art without undue experimentation. In particular embodiments, the resulting fractions of rebaudioside A derivative product may be reprocessed (e.g., using column chromatography or other methods of purification) to further purify the rebaudioside A derivative products. In still other embodiments, the resulting fractions of rebaudioside A derivative product may be concentrated using any suitable concentration method known to those of ordinary skill in the art (e.g., high performance liquid chromatography).

Thus, particular embodiments may comprise rebaudioside A derivative products having a desired level of purity. For example, in one embodiment the rebaudioside A derivative product may comprise from about 50% to about 99.5% by weight of a rebaudioside A derivative compound (on a dry basis), from about 75% to about 99.5%, from about 80% to about 99.5%, from about 85% to about 99.5%, from about 90% to about 99.5%, from about 95% to about 99.5%, from about 97% to about 99.5%, from about 98% to about 99.5%, or from about 99% to about 99.5%.

As used herein, the phrase "rebaudioside A derivative product" is synonymous with "rebaudioside A degradation product" and includes both individual rebaudioside A derivative compounds and combinations of rebaudioside A derivative compounds. For example, particular embodiments of the resulting rebaudioside A derivative products may comprise an individual rebaudioside A derivative compound, a combination of two rebaudioside A derivative compounds, a combination of three rebaudioside A derivative compounds, a combination of four or more rebaudioside A derivative compounds, and the like. The resulting rebaudioside A derivative products also may include residual rebaudioside A (i.e., undegraded rebaudioside A).

II. Rebaudioside A Derivative Products

In particular embodiments, a rebaudioside A derivative compound is provided having the chemical formula I:

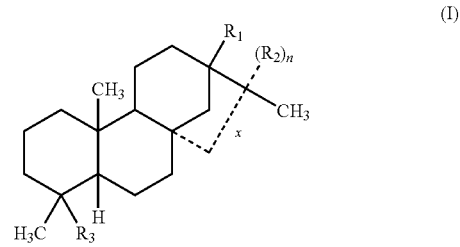

(I)

wherein $R_1$ may be a monosaccharide, an oligosaccharide comprising two or three sugars, an alkyl, or a hydroxyl;

wherein $R_2$ may be a hydrogen, hydroxyl, or alkoxy;

wherein $R_3$ may be a hydrogen, hydroxyl, alkoxy, alkenyl, alkynyl, a straight, chained, branched, or cyclic alkyl, alkenyl, or alkynyl, aryl, heteroaryl, heterocyclic, or acyl group which is substituted or unsubstituted;

wherein x may be a single bond or a double bond;

wherein n is 0 or 1; and wherein when x is a single bond, n is 1, and $R_2$ may be a hydrogen, hydroxyl, or alkoxy; and wherein when x is a double bond, n is 0.

One of ordinary skill in the art should appreciate that embodiments of the rebaudioside A derivative products provided herein may have a plurality of stereocenters as denoted by (R,S) as illustrated with respect to the rebaudioside A derivative compound having the chemical formula I:

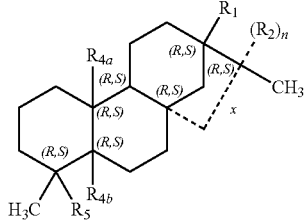

It is envisioned herein that embodiments of rebaudioside A derivative compounds comprising one or more stereocenters, each stereocenter may be in either the R or the S configuration, depending on the arrangement and orientation of the atoms in space. Unless otherwise indicated, it should be understood that the embodiments of rebaudioside A derivative compounds provided herein may comprise any suitable stereochemical configuration. For example, in a particular embodiment, the rebaudioside A derivative compound having the chemical formula I has the following chemical structure:

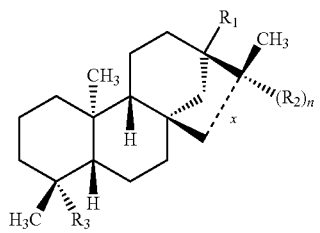

In one embodiment of a rebaudioside A derivative product of formula I, wherein x is a single bond and n is 1, the rebaudioside A derivative compound has the chemical formula IA:

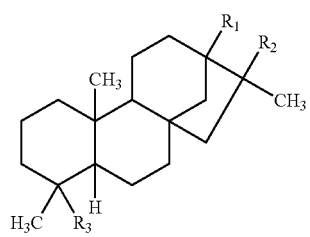

(IA)

wherein $R_1$ may be a monosaccharide, an oligosaccharide comprising two or three sugars, an alkyl, or hydroxyl;

wherein $R_2$ may be a hydrogen, hydroxyl, or alkoxy; and wherein $R_3$ may be a hydrogen, hydroxyl, alkoxy, alkenyl, alkynyl, a straight, chained, branched, or cyclic alkyl, alkenyl, or alkynyl, aryl, heteroaryl, heterocyclic, or acyl group which is substituted or unsubstituted.

In a sub-embodiment of the rebaudioside A derivative compound of formula IA, wherein $R_1$ comprises an oligosaccharide comprising three sugars, $R_2$ comprises a hydroxyl, and $R_3$ comprises a carboxyl-substituted saccharide, the rebaudioside A derivative product comprises a rebaudioside A derivative compound having the chemical formula II:

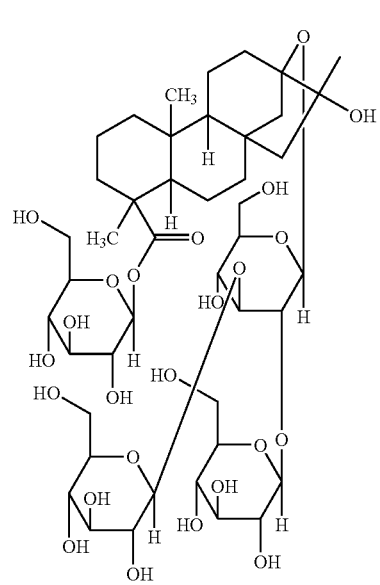

(II)

In another sub-embodiment of the rebaudioside A derivative compound of formula IA, wherein $R_1$ comprises an oligosaccharide comprising three sugars, $R_2$ comprises a hydroxyl, and $R_3$ comprises a carboxyl, the rebaudioside A derivative product comprises a rebaudioside A derivative compound having the chemical formula III:

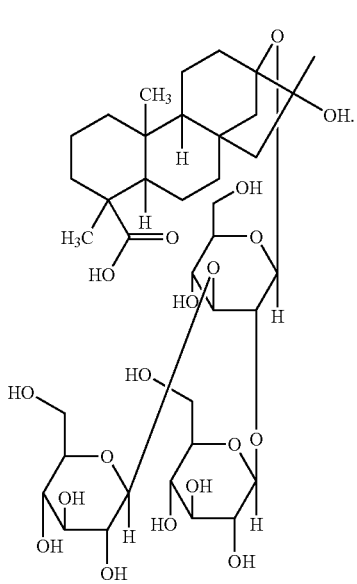

(III)

In one embodiment of a rebaudioside A derivative compound of formula I, wherein x is a double bond and n is 0, the rebaudioside A derivative compound has the chemical formula IB:

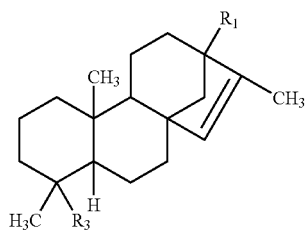

(IB)

wherein $R_1$ may be a monosaccharide, an oligosaccharide comprising two or three sugars, an alkyl, or hydroxyl; and wherein $R_3$ may be a hydrogen, hydroxyl, alkoxy, alkenyl, alkynyl, a straight, chained, branched, or cyclic alkyl, alkenyl, or alkynyl, aryl, heteroaryl, heterocyclic, or acyl group which is substituted or unsubstituted.

In a sub-embodiment of the rebaudioside A derivative product of formula IB, wherein $R_1$ is an oligosaccharide comprising three sugars and $R_3$ comprises a carboxyl-substituted saccharide, the rebaudioside A derivative product comprises a rebaudioside A derivative compound having the chemical formula IV:

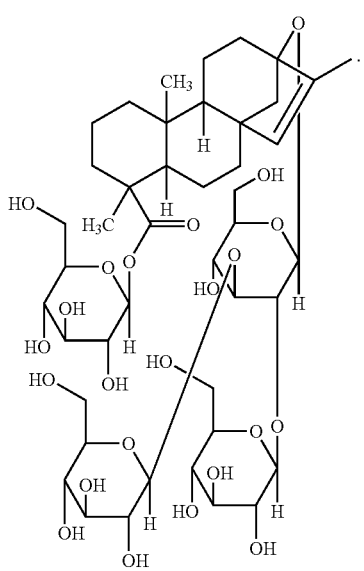

(IV)

In another sub-embodiment of the rebaudioside A derivative product of formula IB, wherein $R_1$ is an oligosaccharide comprising three sugars and $R_3$ is a carboxyl group, the rebaudioside A derivative product comprises a rebaudioside A derivative compound having the chemical formula V:

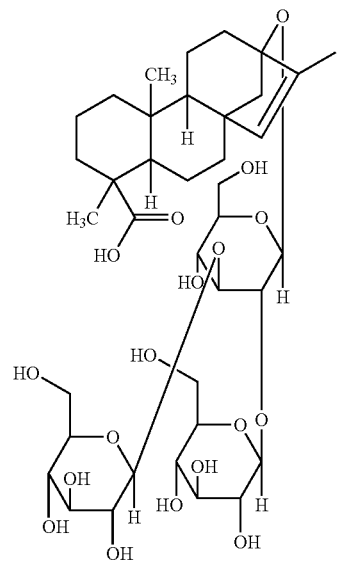

(V)

As described hereinabove, the rebaudioside A derivative products may have any suitable stereochemical configuration known to those of ordinary skill in the art. For example, particular stereochemical configurations of the foregoing compounds having the chemical formulas II, III, IV, and V may comprise compounds having the stereochemical configurations of chemical formulas II', III', IV', and V', respectively:

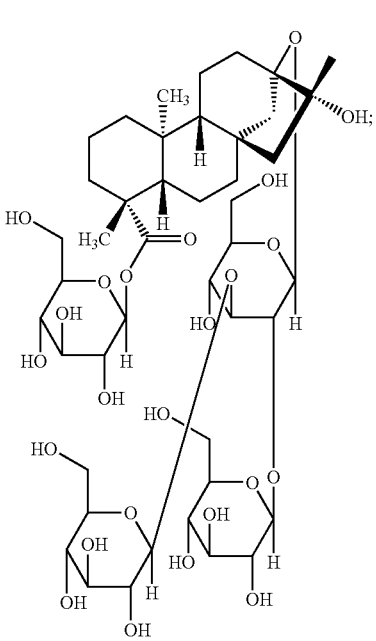

(II')

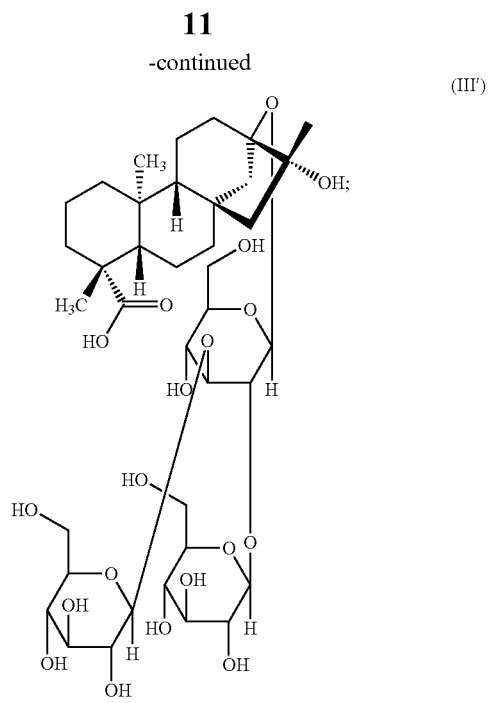

(III')

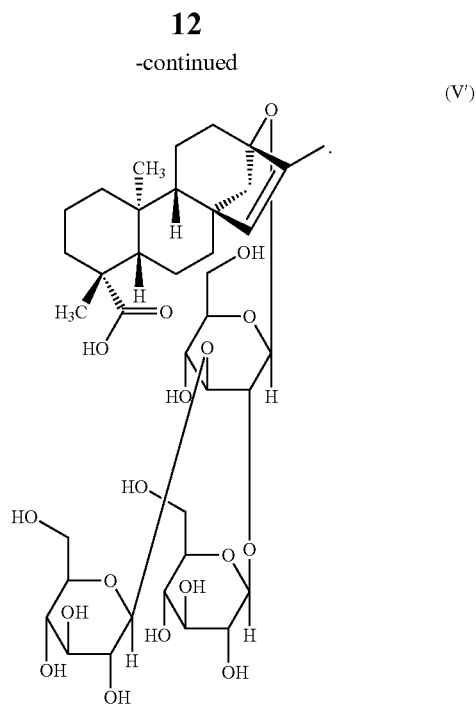

(V')

In another embodiment, the rebaudioside A derivative product comprises a compound having the chemical formula VI:

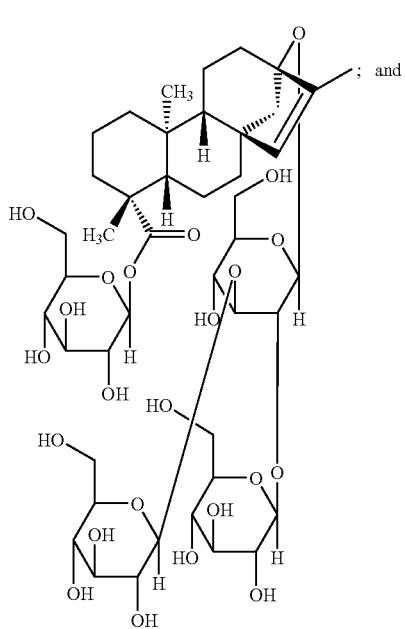

(IV')

; and

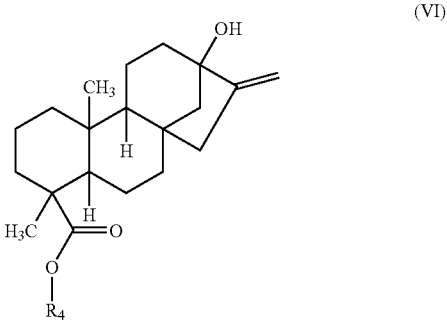

(VI)

wherein $R_4$ may be a monosaccharide.

In a sub-embodiment of the rebaudioside A derivative product of chemical formula VI, wherein $R_4$ is a glucose, the rebaudioside A derivative product comprises a rebaudioside A derivative compound having the chemical formula VII:

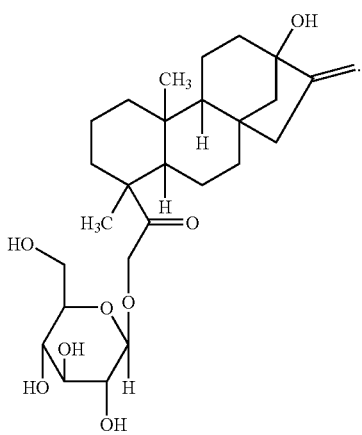
(VII)

In another embodiment, the rebaudioside A derivative product comprises a rebaudioside A derivative compound having the chemical formula VIII:

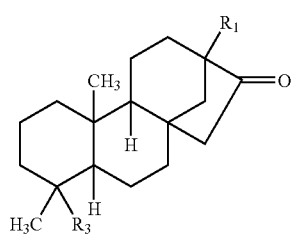
(VIII)

wherein $R_1$ may be a monosaccharide, an oligosaccharide comprising two or three sugars, an alkyl, or a hydroxy; and wherein $R_3$ may be a hydrogen, hydroxyl, alkoxy, alkenyl, alkynyl, a straight, chained, branched, or cyclic alkyl, alkenyl, alkynyl, aryl, heteroaryl, heterocyclic, or acyl group which is substituted or unsubstituted.

In a sub-embodiment of the rebaudioside A derivative product of formula VIII, wherein $R_1$ is a methyl and $R_3$ is glucose, the rebaudioside A derivative product comprises a rebaudioside A derivative compound having the chemical formula IX:

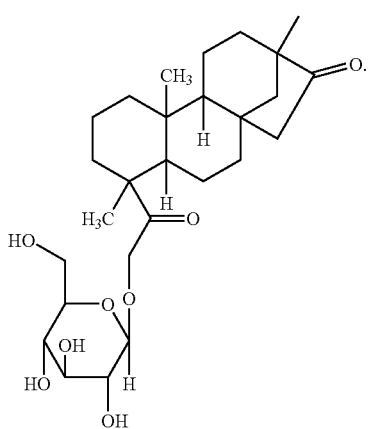
(IX)

In still another embodiment, the rebaudioside A derivative product comprises a rebaudioside A derivative compound having the chemical formula X:

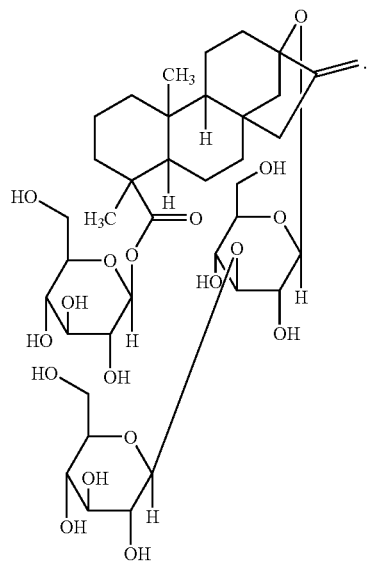
(X)

As described hereinabove, the foregoing rebaudioside A derivative products may have any suitable stereochemical configuration known to those of ordinary skill in the art. For example, particular stereochemical configurations of the compounds having the chemical formulas VII, IX, and X may comprise compounds having the stereochemical configurations of chemical formulas VII', IX', and X', respectively:

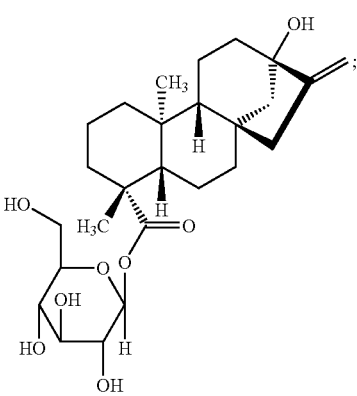
(VII')

-continued

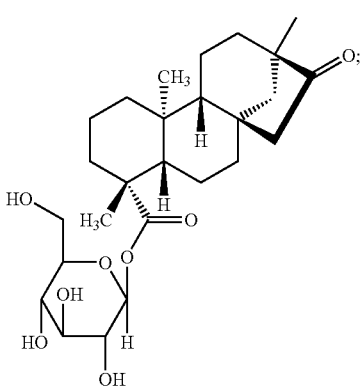

(IX')

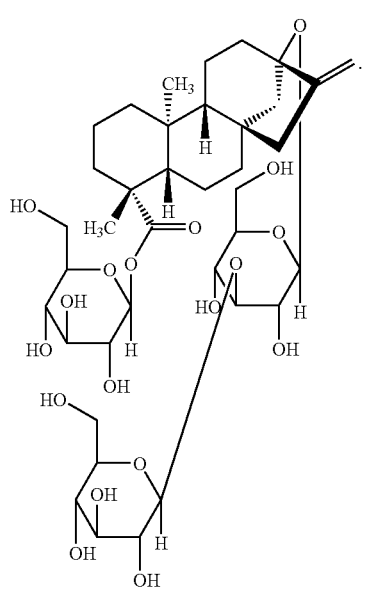

(X')

As previously set forth, particular embodiments may comprise the foregoing rebaudioside A derivative products in any desired level of purity. For example, in one embodiment the rebaudioside A derivative product may comprise any suitable level of purity of the rebaudioside A derivative compound having the chemical formula I, the rebaudioside A derivative compound having the chemical formula II, the rebaudioside A derivative compound having the chemical formula III, the rebaudioside A derivative compound having the chemical formula IV, the rebaudioside A derivative compound having the chemical formula V, the rebaudioside A derivative compound having the chemical formula VI, the rebaudioside A derivative compound having the chemical formula VII, the rebaudioside A derivative compound having the chemical formula VIII, the rebaudioside A derivative compound having the chemical formula IX, the rebaudioside A derivative compound having the chemical formula X, or any combination thereof.

For example, in one embodiment the rebaudioside A derivative product may comprise from about 50% to about 99.5% by weight of the rebaudioside A derivative compound having the chemical formula II (on a dry basis), from about 75% to about 99.5%, from about 80% to about 99.5%, from about 85% to about 99.5%, from about 90% to about 99.5%, from about 95% to about 99.5%, or any amount therebetween. In one embodiment the rebaudioside A derivative product may comprise from about 50% to about 99.5% by weight of the rebaudioside A derivative compound having the chemical formula III (on a dry basis), from about 75% to about 99.5%, from about 80% to about 99.5%, from about 85% to about 99.5%, from about 90% to about 99.5%, from about 95% to about 99.5%, or any amount therebetween. In one embodiment the rebaudioside A derivative product may comprise from about 50% to about 99.5% by weight of the rebaudioside A derivative compound having the chemical formula IV (on a dry basis), from about 75% to about 99.5%, from about 80% to about 99.5%, from about 85% to about 99.5%, from about 90% to about 99.5%, from about 95% to about 99.5%, or any amount therebetween. In one embodiment the rebaudioside A derivative product may comprise from about 50% to about 99.5% by weight of the rebaudioside A derivative compound having the chemical formula V (on a dry basis), from about 75% to about 99.5%, from about 80% to about 99.5%, from about 85% to about 99.5%, from about 90% to about 99.5%, from about 95% to about 99.5%, or any amount therebetween. In one embodiment the rebaudioside A derivative product may comprise from about 50% to about 99.5% by weight of the rebaudioside A derivative compound having the chemical formula VII (on a dry basis), from about 75% to about 99.5%, from about 80% to about 99.5%, from about 85% to about 99.5%, from about 90% to about 99.5%, from about 95% to about 99.5%, or any amount therebetween. In one embodiment the rebaudioside A derivative product may comprise from about 50% to about 99.5% by weight of the rebaudioside A derivative compound having the chemical formula IX (on a dry basis), from about 75% to about 99.5%, from about 80% to about 99.5%, from about 85% to about 99.5%, from about 90% to about 99.5%, from about 95% to about 99.5%, or any amount therebetween. In one embodiment the rebaudioside A derivative product may comprise from about 50% to about 99.5% by weight of the rebaudioside A derivative compound having the chemical formula X (on a dry basis), from about 75% to about 99.5%, from about 80% to about 99.5%, from about 85% to about 99.5%, from about 90% to about 99.5%, from about 95% to about 99.5%, or any amount therebetween.

III. Purification of Rebaudioside A

The rebaudioside A derivative products may be obtained from crude rebaudioside A composition in its raw form as extracted from *Stevia* plants or in purified form. In particular embodiments, the rebaudioside A composition is purified prior to its derivative using methods disclosed in U.S. patent application Ser. No. 11/751,627, filed on May 21, 2007, which claims priority to U.S. Provisional Application No. 60/805,216, filed on Jun. 19, 2006, and 60/889,318, filed on Feb. 12, 2007, the disclosures of which are incorporated herein by reference in their entirety.

Briefly described, crude rebaudioside A composition may be purified by recrystallization. The primary impurities, identified by HPLC, are dulcoside A, stevioside, steviolbioside, rebaudioside B, rebaudioside C, rebaudioside D and rebaudioside F. Rebaudioside D impurity can be removed by increasing the amount of water in an aqueous organic recrystallization solvent; however, excessive water content in the crystallization solvent will result in a lower recovery of rebaudioside A. Rebaudioside B impurity can be reduced significantly by slurrying the crude rebaudioside A composition in an aqueous organic solution or through treatment of the crude rebaudioside A solution with an anion exchange resin. Accordingly, the method of purification depends on the impurities present in the crude rebaudioside A starting material.

In an exemplary embodiment, rebaudioside A composition may be purified by combining crude rebaudioside A composition with an aqueous organic solution to form a rebaudioside A solution. An aqueous organic solution comprises water in an amount from about 10% to about 25% by weight and at least one organic solvent. Alternatively, the aqueous organic solution comprises water in an amount from about 15% to about 20% by weight and at least one organic solvent.

Aqueous organic solvents, as used herein, refer to mixtures of water and at least one organic solvent. Non-limiting examples of organic solvents include alcohol, acetone, and acetonitrile. Alcohol, as used herein, refers to any straight, branched, or cyclic; substituted or unsubstituted alkyl, alkenyl, or alkynyl attached to at least one hydroxyl moiety. Non-limiting examples of alcohols include ethanol, methanol, isopropanol, 1-propanol, 1-butanol, 2-butanol, tert-butanol, and isobutanol.

In an exemplary embodiment, the aqueous organic solution comprises a mixture of water and at least one organic solvent. In another exemplary embodiment, at least one organic solvent comprises an alcohol, the alcohol comprising ethanol, methanol, or mixtures thereof. In exemplary embodiments wherein the at least one organic solvent comprises a mixture of ethanol and methanol, the ethanol and methanol are combined in the aqueous organic solvent in a weight ratio ranging from about 20 parts to about 1 part ethanol to about 1 part methanol. In another exemplary embodiment, the ethanol and methanol are combined in the aqueous organic solvent in a weight ratio ranging from about 3 parts to about 1 part ethanol to about 1 part methanol.

In an exemplary embodiment, the rebaudioside A solution comprises the aqueous organic solvent and the crude rebaudioside A composition in a weight ratio ranging from about 10 to about 4 parts aqueous organic solvent to about 1 part crude rebaudioside A composition. In another exemplary embodiment, the rebaudioside A solution comprises the aqueous organic solution and the crude rebaudioside A composition in a weight ratio ranging from about 5 to about 3 parts aqueous organic solvent to about 1 part crude rebaudioside A composition.

In an exemplary embodiment, the method is carried out at approximately room temperature. In another embodiment, the method further comprises the step of heating the rebaudioside A solution. In an embodiment, the step of heating the rebaudioside A solution comprises heating the rebaudioside A solution to a temperature in a range from about 20° C. to about 70° C., more desirably in a range from about 20° C. to about 50° C., and still more desirably in a range from about 20° C. to about 40° C. In another embodiment, the step of heating the rebaudioside A solution comprises heating the rebaudioside A solution to a reflux temperature. The step of heating the rebaudioside A solution comprises heating the rebaudioside A solution for about 0.25 hours to about 8 hours. In another exemplary embodiment, wherein the method for purifying rebaudioside A comprises the step of heating the rebaudioside A solution, the method further comprises the step of cooling the rebaudioside A solution. In an embodiment, the step of cooling the rebaudioside A solution comprises cooling the rebaudioside A solution to a temperature in the range from about 4° C. to about 25° C. The step of cooling the rebaudioside A solution comprises cooling the rebaudioside A solution for about 0.5 hours to about 24 hours.

The method for purifying rebaudioside A further comprises the step of crystallizing from the rebaudioside A solution in a single step a substantially pure rebaudioside A composition comprising rebaudioside A compound in an amount greater than about 95% by weight on a dry basis. In other exemplary embodiments, substantially pure rebaudioside A composition comprises purity levels of rebaudioside A greater than about 97% rebaudioside A compound by weight on a dry basis, greater than about 98% by weight on a dry basis, or greater than about 99% by weight on a dry basis. The rebaudioside A solution during the single crystallization step may be stirred or unstirred.

In an exemplary embodiment, the method further comprises the step of seeding (optional step) the rebaudioside A solution at an appropriate temperature with substantially pure crystals of rebaudioside A sufficient to promote crystallization of the rebaudioside A to form pure rebaudioside A. An amount of rebaudioside A sufficient to promote crystallization of substantially pure rebaudioside A comprises an amount of rebaudioside A from about 0.0001% to about 1% by weight of the rebaudioside A present in the solution. In another embodiment, an amount of rebaudioside A sufficient to promote crystallization of the rebaudioside A to form a composition of a substantially pure rebaudioside A comprises an amount of rebaudioside A from about 0.01% to about 1% by weight. An appropriate temperature for the step of seeding comprises a temperature in a range from about 18° C. to about 35° C.

In another exemplary embodiment, the method further comprises the steps of separating and washing the substantially pure rebaudioside A composition. The substantially pure rebaudioside A composition may be separated from the aqueous organic solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the rebaudioside A solid-liquid separation device may be continuous, semi-continuous or in batch mode. The substantially pure rebaudioside A composition may also be washed on the separation device using various aqueous organic solvents and mixtures thereof. The substantially pure rebaudioside A composition can be partially and totally dried on the separation device using any number of gases, including, without limitation, nitrogen and argon, to evaporate residual liquid solvent. The substantially pure rebaudioside A composition may be automatically or manually removed from the separation device using liquids, gases or mechanical means by either dissolving the solid or maintaining the solid form.

In still another exemplary embodiment, the method further comprises the step of drying the substantially pure rebaudioside A composition. Such methods are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the step of drying comprises drying the substantially pure rebaudioside A composition using a nitrogen or argon purge to remove the residual solvent at a temperature in a range from about 40° C. to about 60° C. for about 5 hours to about 100 hours.

In yet another exemplary embodiment, wherein the crude rebaudioside A mixture comprises substantially no rebaudioside D impurity, the method further comprises the step of slurrying the composition of substantially pure rebaudioside A with an aqueous organic solvent prior to the step of drying the substantially pure rebaudioside A composition. The slurry is a mixture comprising a solid and an aqueous organic or organic solvent, wherein the solid comprises the substantially pure rebaudioside A composition and is only sparingly soluble in the aqueous organic or organic solvent. In an embodiment, the substantially pure rebaudioside A composition and aqueous organic solvent are present in the slurry in a weight ratio ranging from about 15 parts to about 1 part aqueous organic solvent to about 1 part substantially pure rebaudioside A composition. In one embodiment, the slurry is maintained at room temperature. In another embodiment, the step of slurrying comprises heating the slurry to a temperature in a range from about 20 to about 40° C. The substantially pure rebaudioside A composition is slurried for about 0.5 hours to about 24 hours.

In still yet another exemplary embodiment, the method further comprises the steps of separating the substantially pure rebaudioside A composition from the aqueous organic solvent of the slurry and washing the substantially pure rebaudioside A composition followed by the step of drying the substantially pure rebaudioside A composition.

If further purification is desired, the method of purifying rebaudioside A described herein may be repeated or the substantially pure rebaudioside A composition may be further purified using an alternative purification method, such as the column chromatography.

Purity, as used herein, represents the weight percentage of rebaudioside A present in a rebaudioside A composition in raw or purified form. In one embodiment, a rebaudioside A composition comprises rebaudioside A in a particular purity, with the remainder of the composition comprising a mixture of other steviol glycosides or any component that is not rebaudioside A. The purity of the composition may be measured using methods known to those of ordinary skill in the art. One such method includes high performance liquid chromatography (HPLC). Those of ordinary skill in the art also should appreciate that moisture in the sample may effect the accuracy of purity measurements. Accordingly, it is particularly desirable that the composition be substantially dry. As used herein, a substantially dry composition comprises up to about 10% by weight of moisture.

III. Applications for Rebaudioside A Derivative Products

The rebaudioside A derivative products may be used independently or in combination with appropriate carriers or bulking agents as described in U.S. patent application Ser. No. 11/555,962, filed on Nov. 2, 2006, by Prakash, et al., the disclosure of which is incorporated herein by reference in its entirety. In addition, the temporal and/or flavor profile of the rebaudioside A derivative products may be modified by combining the rebaudioside A derivative products with one or more sweet taste improving compositions to improve the flavor and taste characteristics to be more sugar-like. Combinations of sweeteners and sweet taste improving compositions are described in U.S. patent application Ser. Nos. 11/561,148 and 11/561,158, both filed on Nov. 17, 2006, by Prakash, et al., the disclosures of which are incorporated herein by reference in their entirety. Moreover, the rebaudioside A derivative products may be used either independently or in combination with other natural and/or synthetic sweeteners and optionally sweet taste improving compositions in sweetenable compositions.

As used herein, "orally ingestible composition" and "sweetenable composition" are synonymous and mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range. These compositions include food, beverage, pharmaceutical, tobacco, nutraceutical, oral hygienic/ cosmetic products, and the like. Non-limiting examples of these products include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, café au lait, milk tea, fruit milk beverages, drinkable yogurt, lactic acid bacteria beverages or the like; dairy products; bakery products; desserts such as yogurt, jellies, drinkable jellies, puddings, Bavarian cream, blancmange, cakes, brownies, mousse and the like, sweetened food products eaten at tea time or following meals; frozen foods; cold confections, e.g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); ice cream; general confections, e.g., baked confections or steamed confections such as cakes, crackers, biscuits, buns with bean-jam filling and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans and the like; sauces including fruit flavored sauces, chocolate sauces and the like; edible gels; crèmes including butter crèmes, flour pastes, whipped cream and the like; jams including strawberry jam, marmalade and the like; breads including sweet breads and the like or other starch products; spice; general condiments including seasoned soy sauce used on roasted meats, roast fowl, barbecued meat and the like, as well as tomato catsup, sauces, noodle broth and the like; pet, animal, and veterinary products; processed agricultural products, livestock products or seafood; processed meat products such as sausage and the like; retort food products, pickles, preserves boiled in soy sauce, delicacies, side dishes; snacks such as potato chips, cookies, or the like; cereal products; drugs or quasi-drugs that are administered orally or used in the oral cavity (e.g., vitamins, cough syrups, cough drops, chewable medicine tablets, amino acids, bitter-tasting drug or pharmaceutical agents, acidulants or the like), wherein the drug may be in solid, liquid, gel, or gas form such as a pill, tablet, spray, capsule, syrup, drop, troche agent, powder, and the like; personal care products such as other oral compositions used in the oral cavity such as mouth freshening agents, gargling agents, mouth rinsing agents, toothpaste, tooth polish, dentrifices, mouth sprays, teeth-whitening agents and the like; dietary supplements; tobacco products including smoke and smokeless tobacco products such as snuff, cigarette, pipe and cigar tobacco, and all forms of tobacco such as shredded filler, leaf, stem, stalk, homogenized leaf cured, reconstituted binders and reconstituted tobacco from tobacco dust, fines or ether sources in sheet, pellet or other forms, tobacco substitutes formulated from non-tobacco materials, dip or chewing tobacco; animal feed; and nutraceutical products, which includes any food or part of a food that may provide medicinal or health benefits, including the prevention and treatment of disease (e.g., cardiovascular disease and high levels of cholesterol in the blood, diabetes, osteoporosis, inflammation, or autoimmune disorders).

Generally, the amount of sweetener present in a sweetened composition varies widely depending on the particular type of sweetenable composition and its desired sweetness. Those of ordinary skill in the art can readily discern the appropriate amount of sweetener to put in the sweetenable composition. In particular embodiments, the sweeteners may be added to sweetened compositions in an amount ranging from about 0.5 mg to about 50 mg of sweetener per kilogram or liter of sweetenable composition. In other particular embodiments, those skilled in the art may determine the amount of the rebaudioside A derivative products to attain a desired sweetness using the exemplary sensory data and calculated potencies provided in the accompanying examples hereinbelow.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, %'s are by weight.

EXAMPLES

Example 1

Solutions of rebaudioside A were prepared by dissolving a rebaudioside A composition (5 g, >97% purity) in 0.1 M phosphoric acid solution (200 mL) at pH 2. Prepared solutions were degraded at 80±5° C. for 24 h. Upon degradation, supernatant was decanted from the remaining white precipitate and then clarified with 25-50 mL of methanol (MeOH). The precipitate was separately dissolved in 100 mL of MeOH and was diluted with water to 200 mL total volume prior.

A preliminary analysis of the supernatant and precipitate was made using a Synergi Hydro column maintained at 55° C. and a ternary mobile phase system. The conditions for analysis are summarized in Table 2. HPLC analyses were performed using a Waters 2695 Alliance System coupled to a Waters 996 Photo Diode Array (PDA) detector or an ESA Corona Charged Aerosol Detector (CAD). Final sample analysis was performed using a Phenomenex Synergi Hydro (4.6×250 mm) column.

TABLE 2

Conditions for QC HPLC Method

| Parameter | Description |
|---|---|
| Mobile Phase | 0.1 M ammonium acetate ($NH_4OAc$) (A) |
| | 0.1% (v/v) acetic acid (HOAc) (B) |
| | Acetonitrile (MeCN) (C) |
| Flow Rate (mL/min) | 1 |
| Injection Volume (μL) | 20-100 |
| Detection | UV-Vis, at 210/215 nm or CAD |

TABLE 2-continued

Conditions for QC HPLC Method

| Gradient Description | % A | % B | % C |
|---|---|---|---|
| 0-5 min | 21 | 50 | 29 |
| 5-9 min | 21 | 50-46 | 29-33 |
| 9-29 min | 21 | 46 | 33 |
| 29-39 min | 21-3 | 46-7 | 33-90 |
| 39-43 min | 3 | 7 | 90 |
| 43-43.1 | 3-21 | 7-50 | 90-29 |

The retention times of target components and their relative concentrations upon degradation were determined from the preliminary analysis described above and are summarized in Table 3.

TABLE 3

Derivative Rebaudioside A Sample Composition

| Sample Component | $t_R$ (min) | RRT | Area Percent (%) |
|---|---|---|---|
| Rebaudioside A | 11.00 | 1.0 | 1.2 |
| a | 5.64 | 0.51 | 2.5 |
| b | 11.78 | 1.07 | 29.7 |
| c | 10.78 | 0.98 | 3.3 |
| d | 19.31 | 1.76 | 40.3 |

Supernatant and precipitate isolated from the supernatant and precipitate of the derivative rebaudioside A were processed with a Waters Delta Prep LC Model 2000/4000 coupled to a UV-Vis detector set at 215 nm. Reversed-phase HPLC separations were conducted using a Waters Symmetry C18 (10 μm) column (77×250 mm) with pre-mixed mobile phases (A) 75:25 water/acetonitrile (MeCN) and (B) 60:40 water/MeCN and normal phase separations were performed using two Azko Novel Kromasil Silica (10 μm) columns (77×250 mm and 77×300 mm). The method consisted of a 60-min gradient from 100% A to 100% B with a flow rate of 150 mL/min. Following dissolution of supernatant and precipitate, solutions were injected directly onto the preparative column using an in-line 20 μm stainless steel filter. Three preparative fractions were collected in the purification having the following compositions of analytes: (1) derivative product 1, (2) a mixture of derivative products 2 and 3 and residual rebaudioside A, and (3) a mixture of derivative product 4 and residual rebaudioside A. The chemical structures of the four derivative products are as follows. The first number represents the example identifier (e.g., derivative product 1, 2, 3, or 4) while the roman numeral represents the corresponding chemical formula number set forth hereinabove.

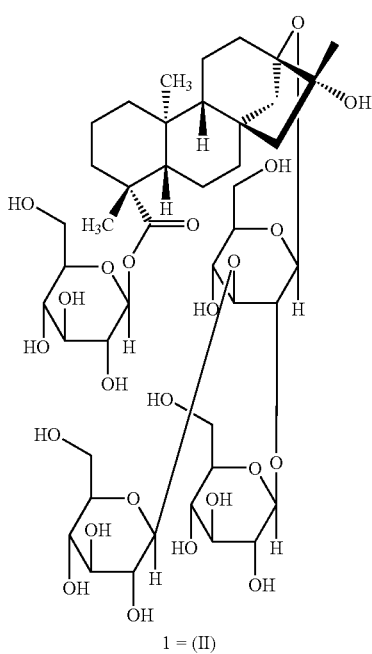

1 = (II)

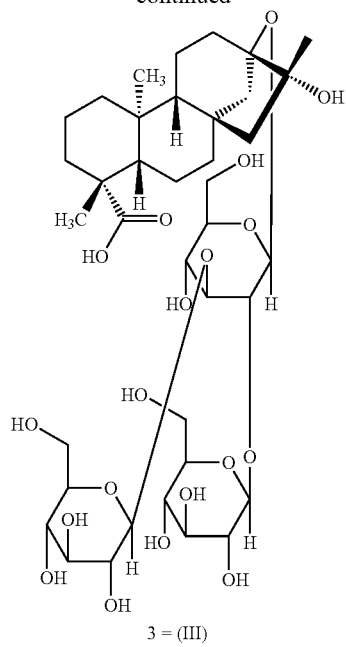

3 = (III)

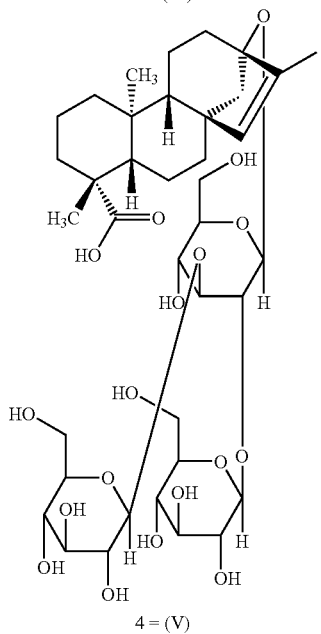

4 = (V)

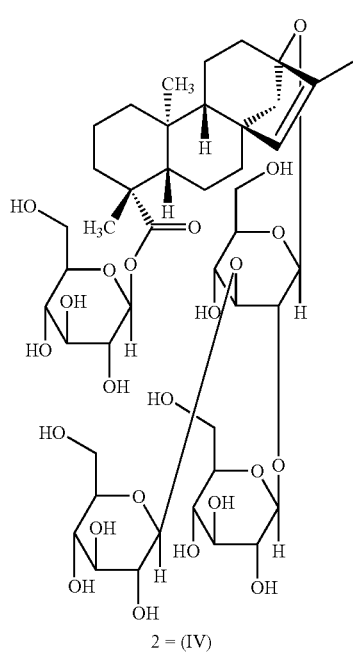

2 = (IV)

Derivative Product 4 was isolated primarily from the precipitate while the remaining analytes (1, 2, and 3) were isolated primarily from the supernatant. Fractions collected from preparative purification were concentrated further by solid phase extraction (SPE). Aqueous solutions were loaded directly onto a 77-mm Symmetry C18 column equilibrated with 95:5 water/MeCN. The column was washed with one column volume of 95:5 water/MeCN and the sample was then eluted from the column in 15:85 water/MeCN. Fractions were subsequently concentrated in vacuo at 30-35° C. using a Buchi Rotary Evaporator model R-114. The samples were lyophilized for a minimum of 12 h using either Kinetics Flexi-Dry Personal or Savant SuperModulo Freeze Dryers.

After purification of each derivative product, each compound was characterized with $^1$H, $^{13}$C, COSY (correlation spectroscopy), and HSQC (heteronuclear single quantum correlation) nuclear magnetic resonance spectroscopy (NMR) and mass spectrometric analysis (MS). The NMR data was generated on a Bruker DRX 500 MHz instrument with an inverse detected capillary probe with a 10 μm flow cell. Samples of each derivative product ranging in size from 100 μg to 0.5 mg were dissolved in 0.5 mL of $CD_3OD$, and the spectra were referenced to the residual solvent signal ($\delta_H$ 3.30, $\delta_C$ 49.0 for $CD_3OD$). The mass spectrometric data were generated with a Sciex API 2000 LC/MS/MS triple quadrupole mass spectrometer equipped with a TurboIonSpray ionization source. Each derivative product was diluted with 1:1:0.01 acetonitrile-$H_2O$-HOAc and introduced via infusion using the onboard syringe pump. The samples were diluted to yield good s/n, typically 0.1 mg/mL.

Purification of Derivative Product 1

The first fraction of analytes obtained using the above-described reversed-phase provided derivative product 1 with purity >95% (area under curve, AUC). The solution was subsequently concentrated in vacuo and lyophilized. Prior to the final lyophilization, the sample was dissolved in 250 mL of 80:20 water/ethanol (EtOH) and filtered through a stainless steel sieve to remove particulate from the sample.

Derivative product 1 was identified as 13-[(2-O-β-D-glucopyranosyl-3-O-β-D-glucopyranosyl-β-D-glucopyranosyl) oxy]-16-hydroxy kauran-18-oic acid β-D-glucopyranosyl ester. $^1H$ NMR (500 MHz, $CD_3OD$) δ 0.86 (m, 1H, $C_1$—H), 0.90 (m, 1H, $C_9$—H), 0.98 (s, 3H, $C_{20}$—H), 1.07 (m, 1H, $C_3$—H), 1.10 (m, 1H, $C_5$—H), 1.20 (s, 3H, $C_{19}$—H), 1.25 (s, 3H, $C_{17}$—H), 1.36 (m, 1H, $C_7$—H), 1.42 (d, J=13.7 Hz, 1H, $C_{15}$—H), 1.43 (m, 1H, $C_2$—H), 1.58 (m, 1H, $C_7$—H), 1.58 (d, J=13.7 Hz, 1H, $C_{15}$—H), 1.64 (m, 1H, $C_{11}$—H), 1.74 (m, 1H, $C_{12}$—H), 1.79 (m, 1H, $C_6$—H), 1.80 (m, 1H, $C_{11}$—H), 1.83 (m, 1H, $C_1$—H), 1.84 (m, 1H, $C_{14}$—H), 1.92 (m, 1H, $C_2$—H), 1.97 (m, 1H, $C_6$—H), 1.98 (m, 1H, $C_{12}$—H), 2.02 (d, J=11.5 Hz, 1H, $C_{14}$—H), 2.05 (d, J=11.9 Hz, 1H, $C_3$—H), 3.15 (m, 1H, $C_{40}$—H), 3.27 (m, 1H, $C_{34}$—H), 3.37 (m, 1H, $C_{22}$—H), 3.65 (m, 1H, $C_{28}$—H), 3.73 (m, 1H, $C_{29}$—H), 4.67 (d, J=7.8 Hz, 1H, $C_{33}$—H), 4.70 (d, J=8.2 Hz, 1H, $C_{27}$—H), 4.88 (d, J=7.8 Hz, 1H, $C_{39}$—H), 5.37 (d, J=8.2 Hz, 1H, $C_{21}$—H); $^{13}C$ NMR (125 MHz, $CD_3OD$) δ 16.0, 19.8, 20.5, 22.1, 22.8, 28.6, 30.6, 38.7, 41.5, 42.3, 43.0, 44.7, 55.7, 56.1, 58.1, 75.1, 75.7, 78.7, 79.9, 87.5, 87.9, 95.4, 96.9, 103.6, 103.9, 178.3; MS (ESI) calculated for $C_{44}H_{72}O_{24}$: 985.03, found: ([M]$^+$) 985.5, ([M]$^-$) 983.6.

Purification of Derivative Products 2 and 3

The second fraction of analytes containing derivative products 2 and 3, and residual rebaudioside A were lyophilized. The lyophiliate was prepared for reprocessing by dissolving 250-mg aliquots into 25 mL of 50:50 water/EtOH. The solutions were processed by a reversed-phase secondary purification using a pre-packed Waters Symmetry C18 column (50×250 mm) and isocratic mobile phase conditions of 73:27 water/MeCN. Flow rate was maintained at 70 mL/min. Three purified fractions were collected from the secondary purification: (1) derivative product 3, (2) undegraded rebaudioside A, and (3) derivative product 2. The isolated derivative product 2 and 3 fractions were concentrated in vacuo and subsequently lyophilized. Prior to the final lyophilization, each sample was dissolved in 150 mL of water and filtered through a stainless steel sieve to remove particulate from the sample.

Derivative product 2 was identified as 13-[(2-O-β-D-glucopyranosyl-3-O-β-D-glucopyranosyl-β-D-glucopyranosyl) oxy]kaur-15-en-18-oic acid β-D-glucopyranosyl ester. $^1H$ NMR (500 MHz, $CD_3OD$) δ 0.85 (m, 1H, $C_1$—H), 0.86 (m, 1H, $C_9$—H), 0.97 (s, 3H, $C_{20}$—H), 1.05 (m, 1H, $C_3$—H), 1.11 (m, 1H, $C_5$—H), 1.21 (s, 3H, $C_{19}$—H), 1.42 (m, 1H, $C_2$—H), 1.48 (m, 1H, $C_7$—H), 1.50 (m, 2H, $C_6$—H, $C_{11}$—H), 1.6 (m, 1H, $C_7$—H), 1.62 (m, 1H, $C_{12}$—H), 1.66 (m, 2H, $C_{11}$—H, $C_{12}$—H), 1.67 (m, 1H, $C_{14}$—H), 1.71 (s, 3H, $C_{17}$—H), 1.83 (m, 1H, $C_6$—H), 1.84 (m, 1H, $C_1$—H), 1.96 (m, 1H, $C_2$—H), 2.13 (d, J=12.2 Hz, 1H, $C_3$—H), 2.22 (d, J=9.6 Hz, 1H, $C_{14}$—H), 3.25 (m, 1H, $C_{40}$—H), 3.27 (m, 1H, $C_{34}$—H), 3.35 (m, 1H, $C_{22}$—H), 3.38 (m, 2H, $C_{30}$—H, $C_{41}$—H), 3.46 (m, 1H, $C_{23}$—H), 3.61 (m, 1H, $C_{28}$—H), 3.73 (m, 1H, $C_{29}$—H), 4.64 (d, J=8.5 Hz, 1H, $C_{27}$—H), 4.66 (d, J=7.8 Hz, 1H, $C_{33}$—H), 4.80 (d, J=8.2 Hz, 1H, $C_{39}$—H), 5.12 (s, 1H, $C_{15}$—H), 5.39 (d, J=8.9 Hz, 1H, $C_{21}$—H); $^{13}C$ NMR (125 MHz, $CD_3OD$) δ 12.1, 15.8, 19.9, 21.5, 28.7, 30.5, 38.8, 40.5, 41.6, 48.4, 48.9, 57.9, 75.2, 79.9, 87.2, 95.4, 96.9, 103.4, 104.0, 136.9; MS (ESI) calculated for $C_{44}H_{70}O_{23}$: 967.01, found: ([M]$^-$ 967.4, ([M]$^-$) 965.8.

Derivative product 3 was identified as 13-[(2-O-β-D-glucopyranosyl-3-O-β-D-glucopyranosyl-β-D-glucopyranosyl) oxy]-16-hydroxy kauran-18-oic acid. $^1H$ NMR (500 MHz, $CD_3OD$) δ 0.86 (m, 1H, $C_1$—H), 0.93 (t, J=7.8 Hz, 1H, $C_9$—H), 0.98 (s, 3H, $C_{20}$—H), 1.0 (m, 1H, $C_3$—H), 1.04 (m, 1H, $C_{12}$—H), 1.07 (m, 1H, $C_5$—H), 1.17 (s, 3H, $C_{19}$—H), 1.27 (s, 3H, $C_{17}$—H), 1.37 (m, 1H, $C_7$—H), 1.42 (m, 1H, $C_2$—H), 1.42 (d, J=13.7 Hz, 1H, $C_{15}$—H), 1.58 (m, 1H, $C_7$—H), 1.60 (d, J=13.7 Hz, 1H, $C_{15}$—H), 1.65 (m, 1H, $C_{11}$—H), 1.8 (m, 1H, $C_{12}$—H), 1.82 (m, 1H, $C_6$—H), 1.84 (m, 1H, $C_{14}$—H), 1.85 (m, 1H, $C_{11}$—H), 1.86 (m, 1H, $C_1$—H), 1.94 (m, 1H, $C_2$—H), 1.97 (m, 1H, $C_6$—H), 1.98 (d, J=10.0 Hz, 1H, $C_{14}$—H), 2.12 (d, J=12.6 Hz, 1H, $C_3$—H), 3.12 (dd, J=8.2 and 8.9 Hz, 1H, $C_{40}$—H), 3.25 (m, 1H, $C_{34}$—H), 3.64 (m, 1H, $C_{28}$—H), 3.74 (t, J=8.5 Hz, 1H, $C_{29}$—H), 4.66 (d, J=7.8 Hz, 1H, $C_{33}$—H), 4.75 (d, J=7.8 Hz, 1H, $C_{27}$—H), 4.91 (d, J=8.2 Hz, 1H, $C_{39}$—H); MS (ESI) calculated for $C_{38}H_{62}O_{19}$: 822.89. found: ([M]$^+$) 823.6, ([M]$^-$) 821.7.

Purification of Derivative Product 4

Upon concentration of the analyte fraction containing derivative product 4 and residual rebaudioside A, a white precipitate formed in solution. The solution was filtered under vacuum using Qualitative Whatman No. 1 filter paper. The filtrand was dried at 40° C. for approximately 5 h. The sample was prepared for reprocessing by dissolving 250-mg aliquots into 13:87 dichloromethane (DCM)/EtOH with sonication. The sample was further diluted to 250 mL with heptane prior to injection. The solutions were processed using a Asko Novel Kromasil Silica (10 μm) Column (77 mm) with isocratic conditions of 70:30 heptane/EtOH with 0.1% acetic acid. Flow rate was maintained at 140 mL/min. The isolated derivative product 4 fractions were concentrated in vacuo and subsequently lyophilized. Prior to the final lyophilization, the sample was dissolved in 350 mL of 13:87 DCM/EtOH and filtered through a stainless steel sieve to remove particulate from the sample.

Derivative product 4 was identified as 13-[(2-O-β-D-glucopyranosyl-3-O-β-D-glucopyranosyl-β-D-glucopyranosyl) oxy]kaur-15-en-18-oic acid. $^1H$ NMR (500 MHz, $CD_3OD$) δ 0.86 (m, 2H, $C_1$—H, $C_9$—H), 0.99 (s, 3H, $C_{20}$—H), 1.02 (m, 1H, $C_3$—H), 1.08 (m, 1H, $C_5$—H), 1.17 (s, 3H, $C_{19}$—H), 1.42 (m, 1H, $C_2$—H), 1.50 (m, 2H, $C_7$—H, $C_{11}$—H), 1.52 (m, 1H, $C_6$—H), 1.58 (m, 1H, $C_7$—H), 1.68 (m, 1H, $C_{12}$—H), 1.69 (m, 1H, $C_{11}$—H), 1.72 (s, 3H, $C_{17}$—H), 1.83 (m, 1H, $C_6$—H), 1.86 (m, 1H, $C_1$—H), 1.90 (m, 1H, $C_2$—H), 2.10 (d, J=11.9 Hz, 1H, $C_3$—H), 2.23 (d, J=10.0 Hz, 1H, $C_{14}$—H), 3.13 (t, J=7.8 Hz, 1H, $C_{40}$—H)), 3.26 (m, 1H, $C_{34}$—H), 3.35 (m, 1H, $C_{41}$—H), 3.39 (m, 1H, $C_{30}$—H), 3.60 (m, 1H, $C_{28}$—H), 3.72 (t, J=7.9 Hz, 1H, $C_{29}$—H), 4.65 (d, J=7.8 Hz, 1H, $C_{33}$—H), 4.66 (d, J=7.8 Hz, 1H, $C_{27}$—H), 4.82 (d, J=7.8 Hz, 1H, $C_{39}$—H), 5.14 (s, 1H, $C_{15}$—H); $^{13}C$ NMR (125 MHz, $CD_3OD$) δ 12.2, 16.1, 19.9, 21.6, 29.0, 30.4, 38.7, 40.4, 41.8, 41.2, 44.4, 47.9, 48.8, 57.4, 70.0, 75.1, 76.0, 80.1, 87.5, 91.4, 96.6, 103.4, 104.0, 137.0, 143.7, 181.4; MS (ESI) calculated for $C_{38}H_{60}O_{18}$: 804.87, found: $([M]^+)$ 805.6, $([M]^-)$ 803.6.

Characterization of Derivative Product Sweetness

These rebaudioside A derivative products were characterized as having an intense sweetening potency. In particular, the sweetness potency of the rebaudioside A derivative products 3 and 4 at 500, 1,000, and 5,000 ppm were determined and found to be about 100 to about 300 times as compared to sucrose at iso-sweetness levels while rebaudioside A derivative products 1 and 2 at 500, 1,000, and 5,000 ppm were found to have about 5 to about 25 times the sweetening potency of sucrose at iso-sweetness levels. In addition, rebaudioside A derivative products 3 and 4 exhibit a sweet clean taste similar to sugar. Thus, the rebaudioside A derivative products are suitable for use as sweeteners for sweetenable compositions.

Example 2

A solution of rebaudioside A (100 mg, >97% purity) was prepared with 0.1 M aqueous phosphoric acid (200 mL) at pH 2. The solution was heated to 80° C. for 24 hours. A sample of the derivative mixture was then analyzed using LC-MS (liquid chromatography-mass spectrometry). The LC-MS analysis was performed with a Sciex API150 EX single quadrupole with an ionspray ionization source operating in positive mode and a Sedere Sedex 75 ELSD (evaporative light scattering detector) operating at 50° C. and 3.5 bar. The LC-MS method, summarized in Table 4, used a Waters $dC_{18}$ (4.6×250 mm, 5 µm) column.

TABLE 4

LC-MS Method Used to Analyze Derivative Mixture

| Mobile Phase | $H_2O$ (0.1% TFA) (A) |
| | Acetonitrile (MeCN) (B) |
| Flow Rate (mL/min) | 1.0 |
| Injection Volume (µL) | 50 |
| Detection | UV-Vis at 220 nm, ELSD, and MSD (+ESI m/z 100-2000) |

| Gradient Description | % A | % B |
| --- | --- | --- |
| 0-14 min | 80 | 20 |
| 15-19 min | 50 | 50 |
| 20-23 min | 10 | 90 |

The ELSD detected single peaks at 10.58, 15.52, and 20.22 minutes, which represented derivative products 1, 4, and 5, respectively. Derivative products 2 and 3 produced a broad and less defined peak at 12.80-13.00 minutes. Subsequent characterization, including the NMR and MS methods described in example 1, confirmed these peak assignments.

The purification of each sample was performed with HPLC. A Phenomenex Prodigy $C_{18}$ (10×250 mm) column (10 µm) was used, and Table 5 summarizes the conditions for the HPLC method. A small scale injection with an ELSD online indicated a chromatographic pattern similar to that observed by LC-MS. For isolation, the ELSD was taken offline and the degradation mixture was dissolved in 15 mL MeCN—$H_2O$ (1:1). The degradation mixture was separated over the course of 8 injections of 2.0 mL each.

TABLE 5

Conditions for HPLC Method for the Isolation of Derivative Product 5

| Mobile Phase | $H_2O$ (0.1% TFA) (A) |
| | Acetonitrile (MeCN) (B) |
| Flow Rate (mL/min) | 5.0 |
| Injection Volume (µL) | 400 |
| Detection | UV-Vis, at 226 nm |

| Gradient Description | % A | % B |
| --- | --- | --- |
| 0-29 min | 95 | 5 |
| 30-35 min | 0 | 100 |

The HPLC method in Table 5 produced only 4 peaks, which appeared at 11.4, 12.9, 14.6, and 18.2 minutes. Subsequent characterization indicated that derivative products 1 and 4 corresponded to the peaks at 11.4 and 14.6 minutes, respectively. 10.6 mg of derivative product 1 and 4.6 mg of derivative product 4 were collected. Derivative product 5 eluted at 18.2 minutes, and 4.2 mg was collected. As described hereinabove, the structure of derivative product 5 was elucidated with NMR and MS. The structure of derivative product 5 was identified as:

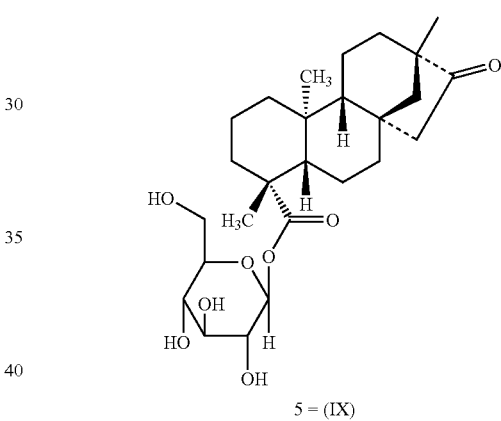

5 = (IX)

Derivative product 5 was identified as 13-methyl-16-oxo-17-norkauran-18-oic acid β-D-glucopyranosyl ester. $^1$H NMR (500 MHz, $CD_3OD$) δ 0.81 (s, 3H, $C_{17}$—H), 0.94 (s, 3H, $C_{20}$—H), 0.97 (m, 1H, $C_1$—H), 1.08 (m, 1H, $C_3$—H), 1.22 (m, 1H, $C_5$—H), 1.23 (m, 4H, $C_{11}$—H, $C_{19}$—H), 1.24 (m, 1H, $C_9$—H), 1.38 (m, 1H, $C_2$—H), 1.43 (m, 1H, $C_{12}$—H), 1.45 (m, 1H, $C_{14}$—H), 1.49 (m, 1H, $C_7$—H), 1.53 (m, 1H, $C_{12}$—H), 1.56 (m, 1H, $C_{14}$—H), 1.68 (m, 2H, $C_7$—H, $C_{11}$—H), 1.71 (m, 1H, $C_1$—H), 1.84 (m, 1H, $C_{15}$—H), 1.90 (m, 3H, $C_2$—H, $C_6$—H), 2.18 (d, J=13.7 Hz, 1H, $C_3$—H), 2.63 (dd, J=3.3, 18.9 Hz, 1H, $C_{15}$—H), 3.33 (m, 1H, $C_{22}$—H), 3.68 (dd, J=3.0, 12.2 Hz, 1H, $C_{26}$—H), 3.82 (d, J=12.2 Hz, 1H, $C_{26}$—H), 5.39 (d, J=8.2 Hz, 1H, $C_{21}$—H); $^{13}$C NMR (125 MHz, $CD_3OD$) δ 13.8, 19.6, 19.9, 21.2, 22.4, 28.8, 38.6, 38.4, 40.6, 42.2, 49.2, 54.9, 55.5, 58.3, 62.2, 95.3 for $C_{26}H_{40}O_8$ $([M]^+)$ 480.59. Found: MS (ESI): $([M]^+)$ 481.1, $([M]^-)$ 479.0.

The HPLC peak at 12.4 minutes represented both derivative products 2 and 3 and undegraded rebaudioside A. Accordingly, a second HPLC method was used to isolate derivative products 2 and 3. The second HPLC method was a modification of the first method described above. The second method used a very shallow gradient of 80:20 (A:B) to 70:30 (A:B) which was applied over 40 minutes. A 10 mg aliquot of the material collected at 12.4 minutes from the first HPLC method was dissolved in 2.0 mL of MeOH and 1.0 mL of this solution was injected per run. Two injections were made and the two peaks observed by ELSD and UV were collected and dried. The peaks at 32.4 and 35.4 minutes corresponded to derivative products 3 and 2, respectively. This second HPLC method yielded 3 mg of derivative product 3 and 3.3 mg of derivative product 2. Subsequent characterization techniques described hereinabove, including NMR and MS, were used to confirm all peak assignments.

Example 3

Mock beverage samples were prepared with rebaudioside A to simulate formulations used in commercial soft drinks. The mock beverages were prepared by combining pre-chilled deionized water, dry ingredients, phosphoric acid, and rebaudioside A (500 mg/L) in a stainless steel kettle with a propeller mixer to a pH 2.8. The mock beverages were then cold-filled into containers, carbonated, and capped. The mock beverage samples were stored at 40° C. for 10 weeks. Storage of the mock beverage samples yielded two additional derivative products: derivative products 6 and 7.

Derivative products 6 and 7 were isolated from the 10-week mock beverage solution by first combining 5 vials of the 10-week mock beverage solution (total volume ~250 mL) and drying the samples with a rotary evaporator operated under reduced pressure. A series of liquid chromatographic steps were used to isolate derivatives products 6 and 7. The concentrated material was dissolved in 6.0 mL of $H_2O$ prior to separation by HPLC. The HPLC analysis was carried out with a Phenomenex Prodigy $C_{18}$ Column (250×10 mm, 10 μm). The conditions for the HPLC analysis are summarized in Table 6.

TABLE 6

Conditions for HPLC Analysis

| Parameter | Description | |
|---|---|---|
| Mobile Phase | $H_2O$ (0.02% HOAc, 0.08% $NH_4OH$) (A) Acetonitrile (B) | |
| Flow Rate (mL/min) | 5.0 | |
| Injection Volume (μL) | 500 | |
| Detection | UV-Vis, at 210 nm | |

| Gradient, Time (min.) | % A | % B |
|---|---|---|
| 0.0 | 75 | 25 |
| 8.5 | 75 | 25 |
| 10.0 | 71 | 29 |
| 15.5 | 70 | 30 |
| 17.5 | 66 | 34 |
| 23.5 | 66 | 34 |
| 25.5 | 48 | 52 |
| 28.5 | 48 | 52 |
| 29.5 | 30 | 70 |
| 35.0 | 30 | 70 |
| 35.1 | 75 | 25 |
| 45.0 | 75 | 25 |
| 46.0 | 75 | 25 |

Derivative product 6 was observed to elute at 20.9 min and derivative product 7 was observed to elute at 28.3 minutes. Both HPLC peaks were collected and dried under $N_2$. Each peak was analyzed with LC-MS. The LC-MS analysis was carried out with a Sciex API150 MCA single quadrupole with an ionspray ionization source operating in negative ion mode. A Sedere Sedex 75 ELS detector was used operating at 50° C. and 3.5 bar. Analysis of the sample was performed using a Phenomenex Synergi Hydro RP column (4.6×250 mm, 4 μm). Table 7 summarizes the LC-MS method.

TABLE 7

LC-MS Method for Derivative Products 6 and 7

| Parameter | Description | |
|---|---|---|
| Mobile Phase | $H_2O$ (5 mM $NH_4OAc$) (A) Acetonitrile (B) | |
| Flow Rate (mL/min) | 1.0 | |
| Injection Volume (μL) | 50 | |
| Detection | UV-Vis, at 220 nm, ELSD, and MSD (−ESI m/z 100-2000) | |

| Gradient, Time (min.) | % A | % B |
|---|---|---|
| 0.0 | 75 | 25 |
| 8.5 | 75 | 25 |
| 10.0 | 71 | 29 |
| 15.5 | 70 | 30 |
| 17.5 | 66 | 34 |
| 23.5 | 66 | 34 |
| 25.5 | 48 | 52 |
| 28.5 | 48 | 52 |
| 29.5 | 30 | 70 |
| 35.0 | 30 | 70 |
| 35.1 | 75 | 25 |
| 45.1 | 75 | 25 |

Although LC-MS confirmed the purity of derivative product 7, derivative product 6 contained residual rebaudioside A. Therefore, a second round of HPLC separation using the same column described above was used to collect a pure sample of derivative product 6. Table 8 summarizes the second HPLC method used to isolate a pure sample of derivative product 6.

TABLE 8

HPLC Method for Isolation of Derivative Product 6

| Parameter | Description | | |
|---|---|---|---|
| Mobile Phase | $H_2O$ (0.08% $NH_4OAc$, 0.02% HOAc) (A) Acetonitrile (MeCN) (B) $H_2O$ (0.05% HOAc) (C) | | |
| Flow Rate (mL/min) | 5.0 | | |
| Injection Volume (μL) | 500 | | |
| Detection | UV-Vis, at 199 nm | | |

| Gradient, Time (min.) | % A | % B | % C |
|---|---|---|---|
| 0.0 | 60 | 25 | 15 |
| 8.5 | 60 | 25 | 15 |
| 10.0 | 57 | 29 | 14 |
| 15.5 | 56 | 30 | 14 |
| 17.5 | 53 | 34 | 13 |
| 23.5 | 53 | 34 | 13 |
| 25.5 | 0 | 52 | 48 |
| 28.5 | 0 | 52 | 48 |
| 29.5 | 0 | 70 | 30 |
| 35.0 | 0 | 70 | 30 |
| 35.1 | 60 | 25 | 15 |
| 45.0 | 60 | 25 | 15 |
| 46.0 | 60 | 25 | 15 |

During the second HPLC analysis, derivative product 6 eluted at 21.2 minutes. The sample was collected and dried for analysis. Derivative products 6 and 7 were characterized with NMR and MS as described hereinabove. The structures of derivative products 6 and 7 were determined to be:

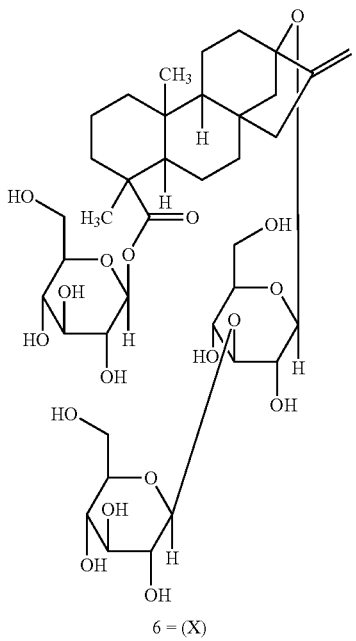

6 = (X)

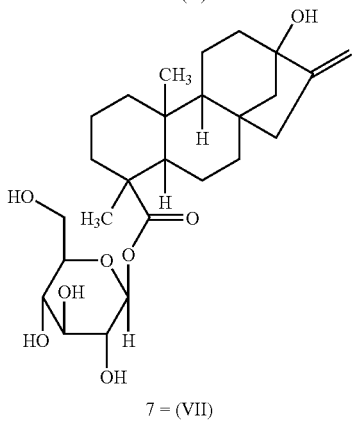

7 = (VII)

Derivative product 6 was identified as 13-[(3-O-β-D-glucopyranosyl-β-D-glucopyranosyl)oxy]kaur-16-en-18-oic acid β-D-glucopyranosyl ester. $^1$H NMR (500 MHz, CD$_3$OD) δ 0.85 (m, 1H, C$_1$—H), 0.98 (m, 1H, C$_9$—H), 0.99 (s, 3H, C$_{20}$—H), 1.06 (m, 1H, C$_3$—H), 1.12 (d, J=11.5 Hz, 1H, C$_5$—H), 1.21 (s, 3H, C$_{19}$—H), 1.42 (m, 1H, C$_2$—H), 1.43 (m, 1H, C$_7$—H), 1.46 (m, 1H, C$_{12}$—H), 1.54 (d, J=12.2 Hz, 1H, C$_{14}$—H), 1.55 (m, 1H, C$_7$—H), 1.67 (m, 1H, C$_{11}$—H), 1.81 (m, 1H, C$_{11}$—H), 1.83 (m, 1H, C$_6$—H), 1.87 (m, 1H, C$_1$—H), 1.94 (m, 1H, C$_2$—H), 2.02 (m, 1H, C$_{12}$—H), 2.05 (m, 1H, C$_{15}$—H), 2.08 (m, 1H, C$_6$—H), 2.14 (d, J=16.3 Hz, 1H, C$_{15}$—H), 2.16 (d, J=12.6 Hz, 1H, C$_3$—H), 2.27 (d, J=12.2 Hz, 1H, C$_{14}$—H), 3.13 (t, J=7.8 Hz, 1H, C$_{40}$—H)), 3.26 (m, 1H, C$_{34}$—H), 3.35 (m, 2H, C$_{22}$—H, C$_{41}$—H), 3.39 (m, 1H, C$_{30}$—H), 3.72 (t, J=7.9 Hz, 1H, C$_{29}$—H), 4.65 (d, J=7.8 Hz, 1H, C$_{33}$—H), 4.82 (s, 1H, C$_{17}$—H, d, J=7.8 Hz, 1H, C$_{39}$—H), 5.11 (s, 1H, C$_{17}$—H), 5.36 (d, J=8.2 Hz, 1H, C$_{21}$—H); $^{13}$C NMR (125 MHz, CD$_3$OD) δ 12.2, 16.1, 19.9, 21.6, 29.0, 30.4, 38.7, 40.4, 41.8, 41.2, 44.4, 47.9, 48.8, 57.4, 70.0, 75.1, 76.0, 80.1, 87.5, 91.4, 96.6, 103.4, 104.0, 137.0, 143.7, 181.4 for C$_{38}$H$_{60}$O$_{18}$ ([M]$^+$) 804.87. Found: MS (ESI): ([M]$^+$) 805.6, (EMI) 8031.6.

Derivative product 7 was identified as 13-hydroxy-kaur-16-en-18-oic acid β-D-glucopyranosyl ester. $^1$H NMR (500 MHz, CD$_3$OD) δ 0.85 (m, 1H, C$_1$—H), 0.98 (m, 1H, C$_9$—H), 0.99 (s, 3H, C$_{20}$—H), 1.06 (m, 1H, C$_3$—H), 1.12 (d, J=11.5 Hz, 1H, C$_5$—H), 1.21 (s, 3H, C$_{19}$—H), 1.42 (m, 1H, C$_2$—H), 1.43 (m, 1H, C$_7$—H), 1.46 (m, 1H, C$_{12}$—H), 1.54 (d, J=12.2 Hz, 1H, C$_{14}$—H), 1.55 (m, 1H, C$_7$—H), 1.67 (m, 1H, C$_{11}$—H), 1.81 (m, 1H, C$_{11}$—H), 1.83 (m, 1H, C$_6$—H), 1.87 (m, 1H, C$_1$—H), 1.94 (m, 1H, C$_2$—H), 2.02 (m, 1H, C$_{12}$—H), 2.05 (m, 1H, C$_{15}$—H), 2.08 (m, 1H, C$_6$—H), 2.14 (d, J=16.3 Hz, 1H, C$_{15}$—H), 2.16 (d, J=12.6 Hz, 1H, C$_3$—H), 2.27 (d, J=12.2 Hz, 1H, C$_{14}$—H), 3.26 (m, 1H, C$_{34}$—H), 3.35 (m, 1H, C$_{22}$—H), 3.37 (m, 1H, C$_{28}$—H), 4.54 (d, J=7.4 Hz, 1H, C$_{27}$—H), 4.56 (d, J=7.4 Hz, 1H, C$_{33}$—H), 4.82 (s, 1H, C$_{17}$—H), 5.11 (s, 1H, C$_{17}$—H), 5.36 (d, J=8.2 Hz, 1H, C$_{21}$—H); $^{13}$C NMR (125 MHz, CD$_3$OD) δ 16.0, 19.9, 22.9, 28.6, 38.7, 41.6, 42.4, 45.0, 48.4, 54.8, 58.4, 95.5, 98.9, 104.6, 105.1; for C$_{38}$H$_{60}$O$_{18}$ ([M]$^+$) 804.87. Found: MS (ESI): ([M]$^-$) 805.3, (EMI) 803.5.

Example 4

The sweetness intensity of the foregoing rebaudioside A derivative products was analyzed by comparing the sweetness intensity of a water sample having a particular amount of sucrose with a second water sample having an identical amount of a rebaudioside A derivative product. The resulting sensory data and calculated potencies are provided in Table 9 below.

TABLE 9

Rebaudioside A Derivative Product Sweetness Intensity

| Sweetener | Amount of Sample (% sucrose or derivative product by weight) | Sweetness Intensity of Derivative Product (as compared to equivalent amount of sucrose) |
|---|---|---|
| Derivative Product 1 (II) | 3.6 | 30 |
| Derivative Product 2 (IV) | 1.1 | 20 |
| Derivative Product 3 (III) | 9.7 | 190 |
| Derivative Product 4 (V) | 6 | 120 |

The sensory data indicated that the rebaudioside A derivative products had sweetness intensities ranging from at least 30 to 120 times that of sucrose. For example, a 3.6 weight percent solution of rebaudioside A derivative product 1 (II) in water is at least 30 times sweeter than a water solution with the same weight percentage of sucrose. Accordingly, it is believed that the derivative products 1 (II), 2 (IV), 3 (III), and 4 (V) may be blended with rebaudioside A, stevioside, or other steviol glycosides to modulate the taste of the sweetener. Derivative products 1 (II), 2 (IV), 3 (III), and 4 (V) also may be blended with other natural non-caloric sweeteners such as mogroside IV, mogroside V, Lo Han Guo sweetener, monatin, thaumatin, brazzein, miraculin, curculin, or mixtures thereof. By combining the rebaudioside A derivative products with these sweeteners, the undesired tastes or aftertastes commonly attributed to these sweeteners may be reduced and/or eliminated.

The quality of sweetness of the rebaudioside A derivative products 1 (II), 2 (IV), 3 (III), and 4 (V) also was evaluated and compared to that of rebaudioside A, rebaudioside B, rebaudioside F, and sucrose at room temperature. For each attribute, the sweeteners received a score based on a 15-point unstructured line scale. Table 10 displays the mean scores and ANOVA results calculated for each attribute after two replications per sweetener. A multiple comparison test, Fisher's LSD 5%, aided in the comparative analysis of the scores. Samples marked with the same letter for a particular attribute were not significantly different at the 95% confidence level.

TABLE 10

Rebaudioside A Derivative Product Sensory Attributes

| Attribute | Sucrose | Rebaudioside A Derivative Products | | | | Comparative Samples | | | p value | LSD Value |
| --- | --- | --- | --- | --- | --- | --- | --- | --- | --- | --- |
| | | 1 (II) | 2 (IV) | 3 (III) | 4 (V) | Reb. A | Reb. B | Reb. F | | |
| Overall Aroma* | 0.40 | 0.17 | 0.09 | 0.09 | 0.19 | 0.16 | 0.28 | 0.29 | 0.73 | 0.380 |
| Sweet Aromatic Aroma* | 0.24 | 0.04 | 0.00 | 0.08 | 0.00 | 0.14 | 0.00 | 0.18 | 0.22 | 0.221 |
| Stale Aroma* | 0.11 | 0.10 | 0.06 | 0.00 | 0.09 | 0.00 | 0.26 | 0.00 | 0.34 | 0.233 |
| Overall Flavor | $10.73^a$ | $3.14^c$ | $3.58^c$ | $10.02^a$ | $6.44^b$ | $9.88^a$ | $4.20^c$ | $5.38^b$ | 0.00 | 1.066 |
| Sweetness | $10.45^a$ | $1.54^d$ | $1.14^d$ | $9.73^a$ | $6.04^b$ | $9.59^a$ | $3.55^c$ | $4.98^b$ | 0.00 | 1.097 |
| Bitterness | $1.47^e$ | $2.28^{bcd}$ | $2.86^{ab}$ | $2.90^{ab}$ | $2.08^{cde}$ | $3.43^a$ | $1.72^{de}$ | $2.64^{bc}$ | 0.00 | 0.644 |
| Sweet Aromatic Flavor | $1.12^a$ | $0.06^c$ | $0.19^{bc}$ | $0.77^{ab}$ | $0.75^{ab}$ | $0.71^{ab}$ | $0.54^{abc}$ | $0.59^{abc}$ | 0.02 | 0.592 |
| Black Licorice Flavor | $0.13^d$ | $0.00^d$ | $0.07^d$ | $1.84^{ab}$ | $1.40^{bc}$ | $2.31^a$ | $0.89^c$ | $0.88^c$ | 0.00 | 0.582 |
| Stale Flavor | 0.50 | 1.01 | 1.21 | 0.63 | 0.77 | 0.89 | 0.92 | 1.14 | 0.17 | 0.549 |
| Metallic Flavor | 1.04 | 0.71 | 0.82 | 1.02 | 0.87 | 0.97 | 0.82 | 1.13 | 0.77 | 0.508 |
| Mouth Numbing | 0.57 | 0.38 | 0.97 | 1.09 | 0.90 | 0.76 | 0.54 | 0.98 | 0.10 | 0.532 |
| Mouthburn | 1.06 | 1.11 | 1.45 | 1.15 | 1.23 | 1.29 | 0.97 | 1.35 | 0.25 | 0.388 |
| Astringency | $3.03^{ab}$ | $2.38^c$ | $2.90^{ab}$ | $3.27^a$ | $3.01^{ab}$ | $3.14^{ab}$ | $2.79^{bc}$ | $3.28^a$ | 0.00 | 0.455 |
| Cooling | $0.38^{bc}$ | $0.29^{bc}$ | $0.12^c$ | $0.57^b$ | $0.70^{ab}$ | $1.10^a$ | $0.57^b$ | $0.57^b$ | 0.00 | 0.443 |
| Overall Aftertaste | $5.05^b$ | $2.18^d$ | $2.35^d$ | $5.72^{ab}$ | $5.24^b$ | $6.34^a$ | $3.54^c$ | $3.89^c$ | 0.00 | 0.823 |
| Sweetness Aftertaste | $4.76^b$ | $0.70^d$ | $0.41^d$ | $5.38^{ab}$ | $4.85^b$ | $5.91^a$ | $3.11^c$ | $3.34^c$ | 0.00 | 0.855 |
| Bitterness Aftertaste | $0.97^d$ | $1.32^{cd}$ | $1.82^{ab}$ | $1.75^{abc}$ | $1.38^{bcd}$ | $2.21^a$ | $1.07^d$ | $1.70^{bc}$ | 0.00 | 0.460 |
| Black Licorice Aftertaste | $0.26^c$ | $0.00^c$ | $0.00^c$ | $1.37^a$ | $1.25^a$ | $1.47^a$ | $0.80^b$ | $0.75^b$ | 0.00 | 0.431 |
| Sweet Aromatic Aftertaste | $1.01^a$ | $0.09^d$ | $0.20^{cd}$ | $0.68^{abc}$ | $0.83^{ab}$ | $0.50^{bcd}$ | $0.46^{bcd}$ | $0.46^{bcd}$ | 0.00 | 0.493 |
| Stale Aftertaste* | 0.58 | 0.56 | 0.74 | 0.41 | 0.47 | 0.48 | 0.63 | 0.81 | 0.53 | 0.414 |
| Metallic Aftertaste | 0.67 | 0.67 | 0.88 | 0.83 | 0.63 | 0.80 | 0.47 | 0.88 | 0.69 | 0.480 |

*More than 50% of the responses for this attribute were zero for all products

As illustrated by the foregoing results, the rebaudioside A derivative products 1 (II), 2 (IV), 3 (III), and 4 (V) have numerous sensory attributes which are not significantly different from sucrose (i.e., both rebaudioside A derivative products 2 (IV) and 4 (V) had 8 characteristics which were not significantly different from sucrose). Most notably, the overall flavor and sweetness of rebaudioside A derivative product 2 (IV) are comparable to sucrose, indicating it likely would be a readily accepted non-caloric sweetener substitute.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A sweetener comprising a compound having the chemical formula:

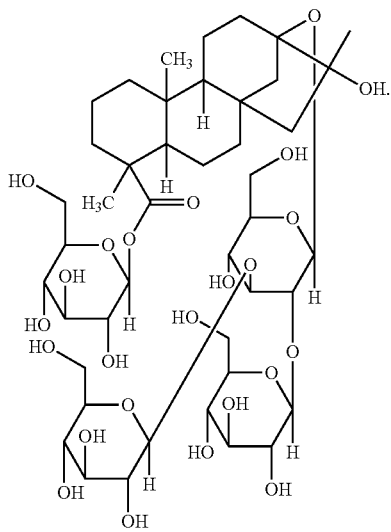

wherein the compound comprises greater than about 50% by weight of the sweetener.

2. A sweetener comprising a compound having the chemical formula:

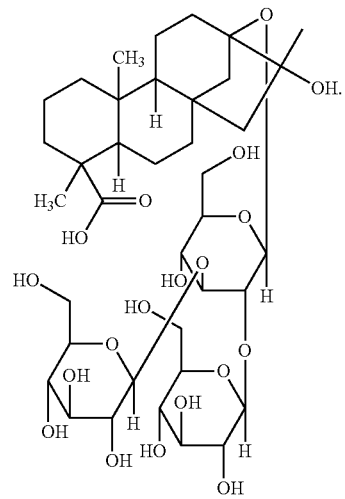

wherein the compound comprises greater than about 50% by weight of the sweetener.

3. The sweetener according to claim 1 or 2, wherein the compound comprises greater than about 75% by weight of the sweetener.

4. The sweetener according to claim 1 or 2, wherein the compound comprises greater than about 85% by weight of the sweetener.

5. The sweetener according to claim 1 or 2, wherein the compound comprises greater than about 95% by weight of the sweetener.

6. The sweetener according to claim 1 or 2, wherein the compound comprises greater than about 97% by weight of the sweetener.

7. The sweetener according to of claim 1 or 2, wherein the compound comprises greater than about 99% by weight of the sweetener.
8. A sweetener according to claim 1, wherein the chemical formula has the following stereochemical configuration:
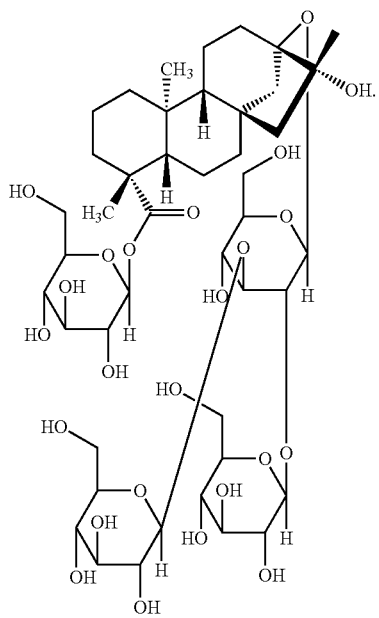
9. A sweetener according to claim 2, wherein the chemical formula has the following stereochemical configuration:
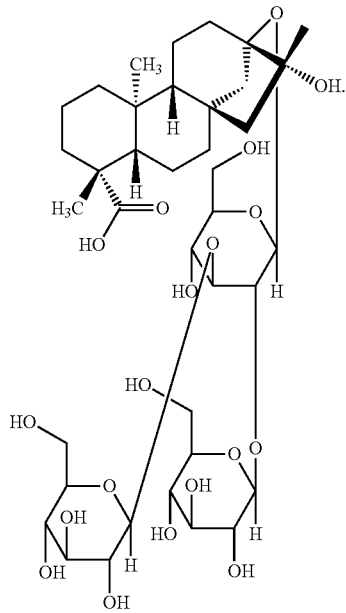
* * * * *